(12) United States Patent
Shanks et al.

(10) Patent No.: US 8,609,110 B2
(45) Date of Patent: Dec. 17, 2013

(54) CITROBACTER FREUNDII ANTIBACTERIAL AGENTS AND THEIR USE

(75) Inventors: Robert M. Q. Shanks, Pittsburgh, PA (US); Daniel E. Kadouri, Livingston, NJ (US)

(73) Assignees: University of Pittsburgh—Of the Commonwealth System of Higher Education, Pittsburgh, PA (US); University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 13/528,633

(22) Filed: Jun. 20, 2012

(65) Prior Publication Data

US 2012/0328684 A1 Dec. 27, 2012

Related U.S. Application Data

(60) Provisional application No. 61/499,675, filed on Jun. 21, 2011.

(51) Int. Cl.
| | |
|---|---|
| *A61K 39/00* | (2006.01) |
| *A61K 39/02* | (2006.01) |
| *A61K 39/38* | (2006.01) |
| *C07K 1/00* | (2006.01) |
| *C07K 14/00* | (2006.01) |
| *C07K 17/00* | (2006.01) |

(52) U.S. Cl.
USPC ............... 424/234.1; 424/184.1; 424/185.1; 530/350

(58) Field of Classification Search
None
See application file for complete search history.

(56) References Cited

U.S. PATENT DOCUMENTS

| 7,592,159 B2 | 9/2009 | Stahl |
|---|---|---|
| 2008/0300169 A1 | 12/2008 | Stahl |
| 2010/0151097 A1 | 6/2010 | Stahl |
| 2010/0168001 A1 | 7/2010 | Hechard et al. |
| 2010/0316643 A1 | 12/2010 | Eckert et al. |
| 2011/0034406 A1 | 2/2011 | Ren et al. |

OTHER PUBLICATIONS

Cascales et al., "Colicin Biology, " *Microbiology and Molecular Biology Reviews*, 71(1): 158-229, 2007.
Cavard et al., "Exclusive Localization of Colicin A in Cell Cytoplasm of Producing Bacteria," *Eur. J. Biochem.*, 119: 125-131, 1981.
GenBank Accession No. X01008, Oct. 23, 2008.
Gordon, "The Potential of Bacteriocin-Producing Probiotics and Associated Caveats," *Future Microbiol.*, 4(8): 941-943, 2009.
Hancock et al., "Probiotic *Escherichia coli* Strain Nissle 1917 Outcompetes Intestinal Pathogens During Biofilm Formation," *Journal of Medical Microbiology*, 59: 392-399, 2010.
Joerger, R.D., "Alternatives to Antibiotics: Bacteriocins, Antimicrobial Peptides and Bacteriophages," *Poult Sci.*, 82(4): 640-647, 2003.
Lazdunski et al., "Colicin Import into *Escherichia coli* Cells," *Journal of Bacteriology*, 180(19): 4993-5002, 1998.
Lewis, "Riddle of Biofilm Resistance," *Antimicrobial Agents and Chemotherapy*, 45(4): 999-1007, 2001.
Majeed et al., "Competitive Interactions in *Escherichia coli* Populations: the Role of Baceteriocins," *The ISME Journal*, pp. 1-11, 2010.
Ong et al., "Molecular Analysis of Type 3 Fimbrial Genes from *Escherichia coli*, *Klebsiella* and *Citrobacter* Species," *BMC Microbiology*, 10: 183, 2010.
Prado et al., "The Evolution of Restraint in Bacterial Biofilms Under Nontransitive Competition," *Evolution*, 62(3): 538-548, 2008.
Shanks et al., "Isolation and Identification of a Baceteriocin with Antibacterial and Antibiofilm Activity from *Citrobacter freundii*," *Arch. Microbiol.*, 13 pages, 2012.
Trautner et al., "Colicins Prevent Colonization of Urinary Catheters," *J. Antimicrob. Chemother.* 56(2): 413-415, 2005.
Varenne et al., "Biosynthesis and Export of Colicin A in *Citrobacter freundii* CA31," *Eur. J. Biochem.*, 116: 615-620, 1981.
Xu et al., "Biofilm Resistance to Antimicrobial Agents," *Microbiology*, 146: 547-549, 2000.

*Primary Examiner* — Oluwatosin Ogunbiyi
(74) *Attorney, Agent, or Firm* — Klarquist Sparkman, LLP

(57) ABSTRACT

Provided herein are methods for treating planktonic bacteria or a biofilm. The methods include contacting the planktonic bacteria or biofilm with an effective amount of an isolated *Citrobacter freundii* colicin A polypeptide, wherein the polypeptide has an antibacterial activity against the planktonic bacteria or the biofilm. Methods are also provided herein for treating a subject that has a bacterial infection, for example caused by a biofilm. The methods can be used to treat a biofilm on a living or non-living surface. Also provided herein are *Citrobacter freundii* colicin A polypeptides that have an antibacterial activity against planktonic bacteria or surface attached bacteria, and nucleic acid sequences encoding the polypeptides. Medical devices comprising a surface having an antimicrobial effective amount of a *Citrobacter freundii* colicin A polypeptide, or a nucleic acid molecule encoding the polypeptide, are also disclosed.

28 Claims, 8 Drawing Sheets

FIG. 1A  I  II
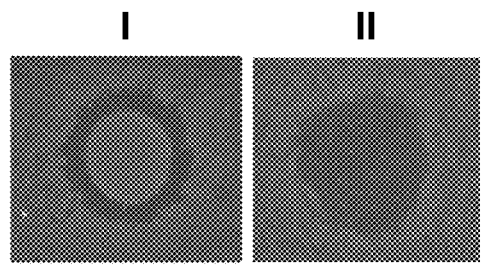
FIG. 1B
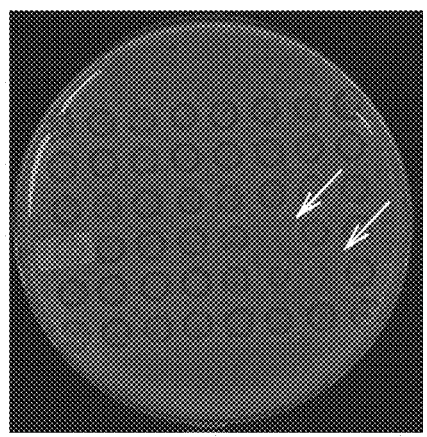
FIG. 1C  I  II
*C. freundii*
43864 Wild-
type
*Cf-8A*
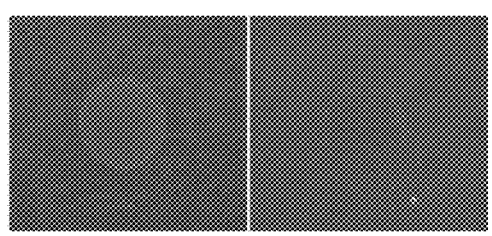

C. freundii NCTC 9750 Wild-type | C. freundii NCTC 9750 -8A
C. freundii ATCC 8090 Wild-type | C. freundii ATCC 8090 - 8A
E. Coli S17 Wild type | E. Coli S17 - 8A plasmid
E. Coli S17-pMQ124 | E. coli S17-pMQS345

SEQUENCE LISTING

```
<160> NUMBER OF SEQ ID NOS: 18

<210> SEQ ID NO 1
<211> LENGTH: 592
<212> TYPE: PRT
<213> ORGANISM: Citrobacter freundii

<400> SEQUENCE: 1

Met Pro Gly Phe Asn Tyr Gly Gly Lys Gly Asp Gly Thr Gly Trp Ser
1               5                   10                  15

Ser Glu Arg Gly Ser Gly Pro Glu Pro Gly Gly Gly Ser His Gly Asn
            20                  25                  30

Ser Gly Gly His Asp Arg Gly Asp Ser Ser Asn Val Gly Asn Glu Ser
        35                  40                  45

Val Thr Val Met Lys Pro Gly Asp Ser Tyr Asn Thr Pro Trp Gly Lys
    50                  55                  60

Val Ile Ile Asn Ala Ala Gly Gln Pro Thr Met Asn Gly Thr Val Met
65                  70                  75                  80

Thr Ala Asp Asn Ser Ser Met Val Pro Tyr Gly Arg Gly Phe Thr Arg
                85                  90                  95

Val Leu Asn Ser Leu Val Asn Asn Pro Val Ser Pro Ala Gly Gln Asn
            100                 105                 110

Gly Gly Lys Ser Pro Val Gln Thr Ala Val Glu Asn Tyr Leu Met Val
        115                 120                 125

Gln Ser Gly Asn Leu Pro Pro Gly Tyr Trp Leu Ser Asn Gly Lys Val
    130                 135                 140

Met Thr Glu Val Arg Glu Glu Arg Thr Ser Gly Gly Gly Lys Asn
145                 150                 155                 160

Gly Asn Glu Arg Thr Trp Thr Val Lys Val Pro Arg Glu Val Pro Gln
                165                 170                 175

Leu Thr Ala Ser Tyr Asn Glu Gly Met Arg Ile Arg Gln Glu Ala Ala
            180                 185                 190

Asp Arg Ala Arg Ala Glu Ala Asn Ala Arg Ala Leu Ala Glu Glu Glu
        195                 200                 205

Ala Arg Ala Ile Ala Ser Gly Lys Ser Lys Ala Glu Phe Asp Ala Gly
    210                 215                 220
```

```
Lys Arg Val Glu Ala Ala Gln Ala Ala Ile Asn Thr Ala Gln Leu Asn
225                 230                 235                 240

Val Asn Asn Leu Ser Gly Ala Val Ser Ala Asn Gln Val Ile Thr
            245                 250                 255

Gln Lys Gln Ala Glu Met Thr Pro Leu Lys Asn Glu Leu Ala Ala Ala
            260                 265                 270

Asn Gln Arg Val Gln Glu Thr Leu Lys Phe Ile Asn Asp Pro Ile Arg
            275                 280                 285

Ser Arg Ile His Phe Asn Met Arg Ser Gly Leu Ile Arg Ala Gln His
        290                 295                 300

Asn Val Asp Thr Lys Gln Asn Glu Ile Asn Ala Val Ala Asn Arg
305                 310                 315                 320

Asp Ala Leu Asn Ser Gln Ser Ser Gln Ala Asn Asn Ile Leu Gln Asn
                325                 330                 335

Ala Arg Asn Glu Lys Ser Ala Ala Asp Ala Ala Leu Ser Ala Ala Thr
            340                 345                 350

Ala Gln Arg Leu Gln Ala Glu Ala Ala Leu Arg Ala Ala Glu Ala
            355                 360                 365

Ala Glu Lys Ala Arg Gln Arg Gln Ala Glu Gly Ala Glu Arg Gln
370                 375                 380

Gln Ala Met Glu Val Ala Glu Lys Ala Lys Asp Glu Arg Glu Leu Leu
385                 390                 395                 400

Glu Lys Thr Ser Glu Leu Ile Ala Gly Met Gly Asp Lys Ile Gly Glu
                405                 410                 415

His Leu Gly Asp Lys Tyr Lys Ala Ile Ala Lys Asp Ile Ala Asp Asn
            420                 425                 430

Ile Lys Asn Phe Gln Gly Lys Thr Ile Arg Ser Phe Asp Asp Ala Met
        435                 440                 445

Ala Ser Leu Asn Lys Ile Thr Ala Asn Pro Ala Met Lys Ile Asn Lys
450                 455                 460

Ala Asp Arg Asp Ala Leu Val Asn Ala Trp Lys His Val Asp Ala Gln
465                 470                 475                 480

Asp Met Ala Asn Lys Leu Gly Asn Leu Ser Lys Ala Phe Lys Val Ala
                485                 490                 495

Asp Val Val Met Lys Val Glu Lys Val Arg Glu Lys Ser Ile Glu Gly
            500                 505                 510

Tyr Glu Thr Gly Asn Trp Gly Pro Leu Met Leu Glu Val Glu Ser Trp
            515                 520                 525

Val Leu Ser Gly Ile Ala Ser Ser Val Ala Leu Gly Ile Phe Ser Ala
530                 535                 540

Thr Leu Gly Ala Tyr Ala Leu Ser Leu Gly Val Pro Ala Ile Ala Val
545                 550                 555                 560

Gly Ile Ala Gly Ile Leu Leu Ala Ala Val Val Gly Ala Leu Ile Asp
                565                 570                 575

Asp Lys Phe Ala Asp Ala Leu Asn Asn Glu Ile Ile Arg Pro Ala His
            580                 585                 590

<210> SEQ ID NO 2
<211> LENGTH: 1779
<212> TYPE: DNA
<213> ORGANISM: Citrobacter freundii

<400> SEQUENCE: 2
atgcctggat ttaattatgg tggaaaaggt gatggaaccg gctggagctc agaacgtggg      60
agtggtccag agccgggtgg tgtagccat ggaaatagtg gtgggcacga tcgtggagat     120
```

-continued

```
tcttccaacg taggtaatga gtctgtgacg gtaatgaaac caggggattc gtataacacc    180
ccgtggggaa aagtcatcat caatgctgca ggccagccga ccatgaacgg aacggtgatg    240
accgctgata attcatcgat ggttccttac ggcagagggt ttacacgggt tttaaattcc    300
ctggtcaata atcctgtttc gccggcaggt cagaatggcg ggaagtctcc tgttcagact    360
gctgtggaaa attatctgat ggtacagtca ggaaacctgc caccgggcta ctggctcagt    420
aatggcaagg ttatgacgga ggttcgtgag aacgtactt ctggcggcgg tgggaaaaac    480
gggaacgagc gaacctggac tgtgaaagtt ccccgggaag tacctcagct tacggcatcc    540
tataacgagg ggatgagaat ccgacaggag gcagctgacc gtgccagagc ggaagcaaat    600
gcccgcgctc tggctgaaga ggaagcccgt gccatcgcat caggaaagag caaagctgag    660
tttgatgcag gtaagcgggt ggaggccgca caggcagcga ttaatacagc acaactcaat    720
gttaataacc tcagcggcgc tgtcagtgct gcaaatcagg ttataactca gaaacaggct    780
gaaatgacgc ccctgaaaaa tgagcttgca gccgctaacc agcgtgtcca ggagacgctt    840
aaatttatca atgatcctat tcgtagccgg attcatttta atatgcgaag tggcctgatt    900
cgcgctcaac ataacgttga tactaaaacag aatgaaatta atgcagcagt ggctaaccgt    960
gatgctctga atagccaatc gtctcaggct aataatatcc tgcagaatgc ccggaacgaa    1020
aagagtgcgg ctgatgcagc actttcagct gccacagcac agcggttaca ggcagaagcc    1080
gcactcaggg ctgctgctga ggctgcagaa aaagcgcgcc agcgccaggc tgaagaagcc    1140
gaacgtcagc gtcaggctat ggaagttgcg gaaaaagcca agatgagcg ggagctgctt    1200 gaaaaaacca gtgaactgat tgctggtatg ggagataaaa tcggcgagca tcttggagat    1260
aaatataagg cgatagcgaa agatattgcg gacaatatta aaaattttca ggggaagacc    1320
atccgtagct ttgatgatgc aatggcatcg ctgaataaaa tcacagccaa cccagccatg    1380
aaaattaata aggcggacag agatgctctg gttaatgcct ggaaacatgt tgatgctcag    1440
gatatggcga ataaactggg taatctcagc aaggctttta aagtcgccga cgtggtgatg    1500
aaggttgaga aggtccggga gaagagcatt gaggggtatg aaaccgggaa ctggggccg    1560 ctgatgctgg aggtggaatc ctgggtgctc agtggtatag cttcctctgt tgctctgggg    1620
attttttccg ctacattagg agcatatgcc ttatctcttg gagttcctgc tattgctgtt    1680
ggtatcgccg gtattctact cgcagcagtt gttggtgcgt taattgatga taagtttgca    1740
gatgctttga ataatgaaat aatccgacct gcacattaa                          1779
```

<210> SEQ ID NO 3
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 3

```
acaggaaaca ggactctaga gg                                              22
```

<210> SEQ ID NO 4
<211> LENGTH: 35
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (21)..(30)
<223> OTHER INFORMATION: n is a, c, g, or t

<400> SEQUENCE: 4
ggccacgcgt cgactagtac nnnnnnnnnn gatat                                    35

<210> SEQ ID NO 5
<211> LENGTH: 35
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (21)..(30)
<223> OTHER INFORMATION: n is a, c, g, or t

<400> SEQUENCE: 5
ggccacgcgt cgactagtac nnnnnnnnnn acgcc                                    35

<210> SEQ ID NO 6
<211> LENGTH: 34
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (21)..(30)
<223> OTHER INFORMATION: n is a, c, g, or t

<400> SEQUENCE: 6
ggccacgcgt cgactagtac nnnnnnnnnn agag                                     34

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
ggccacgcgt cgactagtac                                                     20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 8
cacccagctt tcttgtacac                                                     20

<210> SEQ ID NO 9
<211> LENGTH: 77
<212> TYPE: DNA
<213> ORGANISM: Artificial Sequence
<220> FEATURE:
<223> OTHER INFORMATION: Oligonucleotide primer

<400> SEQUENCE: 9
accgcttctg cgttctgatt taatctgtat cattagtgat ggtggtgatg gtggtgatgt         60
gcaggtcgga ttatttc                                                        77

<210> SEQ ID NO 10
<211> LENGTH: 60
<212> TYPE: DNA
<213> ORGANISM: Artificial Sequence -continued

```
<220> FEATURE:
<223> OTHER INFORMATION: Oligonucleotide primer

<400> SEQUENCE: 10
ctctctactg tttctccata cccgtaggag gaaaaagaat gcctggattt aattatggtg    60

<210> SEQ ID NO 11
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 11
cgttgtaaaa cgacggccag tgccaagctt gcatgcctgc gtttgattaa aaggcagtgt    60

<210> SEQ ID NO 12
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 12
gaattgtgag cggataacaa tttcacacag gaaacatatg aatgaacact caatagatac    60

<210> SEQ ID NO 13
<211> LENGTH: 592
<212> TYPE: PRT
<213> ORGANISM: Citrobacter freundii

<400> SEQUENCE: 13
```

Met Pro Gly Phe Asn Tyr Gly Gly Lys Gly Asp Gly Thr Gly Trp Ser
1               5                   10                  15

Ser Glu Arg Gly Ser Gly Pro Glu Pro Gly Gly Gly Ser His Gly Asn
            20                  25                  30

Ser Gly Gly His Asp Arg Gly Asp Ser Ser Asn Val Gly Asn Glu Ser
        35                  40                  45

Val Thr Val Met Lys Pro Gly Asp Ser Tyr Asn Thr Pro Trp Gly Lys
    50                  55                  60

Val Ile Ile Asn Ala Ala Gly Gln Pro Thr Met Asn Gly Thr Val Met
65                  70                  75                  80

Thr Ala Asp Asn Ser Ser Met Val Pro Tyr Gly Arg Gly Phe Thr Arg
                85                  90                  95

Val Leu Asn Ser Leu Val Asn Asn Pro Val Ser Pro Ala Gly Gln Asn
            100                 105                 110

Gly Gly Lys Ser Pro Val Gln Thr Ala Val Glu Asn Tyr Leu Met Val
        115                 120                 125

Gln Ser Gly Asn Leu Pro Pro Gly Tyr Trp Leu Ser Asn Gly Lys Val
    130                 135                 140

Met Thr Glu Val Arg Glu Arg Thr Ser Gly Gly Gly Lys Asn
145                 150                 155                 160

Gly Asn Glu Arg Thr Trp Thr Val Lys Val Pro Arg Glu Val Pro Gln
                165                 170                 175

Leu Thr Ala Ser Tyr Asn Glu Gly Met Arg Ile Arg Gln Glu Ala Ala
            180                 185                 190

Asp Arg Ala Arg Ala Glu Ala Asn Ala Arg Ala Leu Ala Glu Glu Glu
        195                 200                 205

Ala Arg Ala Ile Ala Ser Gly Lys Ser Lys Ala Glu Phe Asp Ala Gly
    210                 215                 220

| | | | | | | | | | | | | |
|---|---|---|---|---|---|---|---|---|---|---|---|---|
| Lys | Arg | Val | Glu | Ala | Ala | Gln | Ala | Ala | Ile | Asn | Thr | Ala | Gln | Leu | Asn |
| 225 | | | | 230 | | | | | 235 | | | | 240 |

Val Asn Asn Leu Ser Gly Ala Val Ser Ala Ala Asn Gln Val Ile Thr
                    245                 250                 255

Gln Lys Gln Ala Glu Met Thr Pro Leu Lys Asn Glu Leu Ala Ala Ala
            260                 265                 270

Asn Gln Arg Val Gln Glu Thr Leu Lys Phe Ile Asn Asp Pro Ile Arg
        275                 280                 285

Ser Arg Ile His Phe Asn Met Arg Ser Gly Leu Ile Arg Ala Gln His
    290                 295                 300

Asn Val Asp Thr Lys Gln Asn Glu Ile Asn Ala Val Ala Asn Arg
305                 310                 315                 320

Asp Ala Leu Asn Ser Gln Leu Ser Gln Ala Asn Asn Ile Leu Gln Asn
                325                 330                 335

Ala Arg Asn Glu Lys Ser Ala Ala Asp Ala Ala Leu Ser Ala Ala Thr
            340                 345                 350

Ala Gln Arg Leu Gln Ala Glu Ala Ala Leu Arg Ala Ala Glu Ala
        355                 360                 365

Ala Glu Lys Ala Arg Gln Arg Gln Ala Glu Ala Glu Arg Gln Arg
    370                 375                 380

Gln Ala Met Glu Val Ala Glu Lys Ala Lys Asp Glu Arg Glu Leu Leu
385                 390                 395                 400

Glu Lys Thr Ser Glu Leu Ile Ala Gly Met Gly Asp Lys Ile Gly Glu
                405                 410                 415

His Leu Gly Asp Lys Tyr Lys Ala Ile Ala Lys Asp Ile Ala Asp Asn
            420                 425                 430

Ile Lys Asn Phe Gln Gly Lys Thr Ile Arg Ser Phe Asp Asp Ala Met
        435                 440                 445

Ala Ser Leu Asn Lys Ile Thr Ala Asn Pro Ala Met Lys Ile Asn Lys
    450                 455                 460

Ala Asp Arg Asp Ala Leu Val Asn Ala Trp Lys His Val Asp Ala Gln
465                 470                 475                 480

Asp Met Ala Asn Lys Leu Gly Asn Leu Ser Lys Ala Phe Lys Val Ala
                485                 490                 495

Asp Val Val Met Lys Val Glu Lys Val Arg Glu Lys Ser Ile Glu Gly
            500                 505                 510

Tyr Glu Thr Gly Asn Trp Gly Pro Leu Met Leu Glu Val Glu Ser Trp
        515                 520                 525

Val Leu Ser Gly Ile Ala Ser Ser Val Ala Leu Gly Ile Phe Ser Ala
    530                 535                 540

Thr Leu Gly Ala Tyr Ala Leu Ser Leu Gly Val Pro Ala Ile Ala Val
545                 550                 555                 560

Gly Ile Ala Gly Ile Leu Leu Ala Ala Val Val Gly Ala Leu Ile Asp
                565                 570                 575

Asp Lys Phe Ala Asp Ala Leu Asn Asn Glu Ile Ile Arg Pro Ala His
            580                 585                 590

<210> SEQ ID NO 14
<211> LENGTH: 2123
<212> TYPE: DNA
<213> ORGANISM: Citrobacter freundii

<400> SEQUENCE: 14
gacagcatgg aactgccggg cgtagtatca ttttactgta tataaacaca tgtgaatata     60
tacagttttt ggtgtggcag agcacttata acagcgtggc ggcaggtagc cgctcagcaa    120

```
taaaccgcac accagatttc tcataaaaca aaaataaaaa gaggaaagat tatgcctgga      180
tttaattatg gtggaaaagg tgatggaacc ggctggagct cagaacgtgg gagtggtcca      240
gagccgggtg gtggtagcca tggaaatagt ggtgggcacg atcgtggaga ttcttccaac      300
gtaggtaatg agtctgtgac ggtaatgaaa ccaggggatt cgtataacac cccgtgggga      360
aaagtcatca tcaatgctgc aggccagccg accatgaacg gaacggtgat gaccgctgat      420
aattcatcga tggttcctta cggcagaggg tttacacggg ttttaaattc cctggtcaat      480
aatcctgttt cgccggcagg tcagaatggc gggaagtctc ctgttcagac tgctgtggaa      540
aattatctga tggtacagtc aggaaacctg ccaccgggct actggctcag taatggcaag      600
gttatgacgg aggttcgtga ggaacgtact tctggcggcg gtgggaaaaa cgggaacgag      660
cgaacctgga ctgtgaaagt tccccgggaa gtacctcagc ttacggcatc ctataacgag      720
gggatgagaa tccgacagga ggcagctgac cgtgccagag cggaagcaaa tgcccgcgct      780
ctggctgaag aggaagcccg tgccatcgca tcaggaaaga gcaaagctga gtttgatgca      840
ggtaagcggg tggaggccgc acaggcagcg attaatacag cacaactcaa tgttaataac      900
ctcagcggcg ctgtcagtgc tgcaaatcag gttataactc agaaacaggc tgaaatgacg      960
cccctgaaaa atgagcttgc agccgctaac cagcgtgtcc aggagacgct taaatttatc     1020
aatgatccta ttcgtagccg gattcatttt aatatgcgaa gtggcctgat tcgcgctcaa     1080
cataacgttg atactaaaca gaatgaaatt aatgcagcag tggctaaccg tgatgctctg     1140
aatagccaat tgtctcaggc taataatatc ctgcagaatg cccggaacga aaagagtgcg     1200
gctgatgcag cactttcagc tgccacagca cagcggttac aggcagaagc cgcactcagg     1260
gctgctgctg aggctgcaga aaaagcgcgc cagcgccagg ctgaagaagc cgaacgtcag     1320
cgtcaggcta tggaagttgc ggaaaaagcc aaagatgagc gggagctgct tgaaaaaacc     1380
agtgaactga ttgctggtat gggagataaa atcggcgagc atcttggaga taaatataag     1440
gcgatagcga aagatattgc ggacaatatt aaaaattttc aggggaagac catccgtagc     1500
tttgatgatg caatggcatc gctgaataaa atcacagcca acccagccat gaaaattaat     1560
aaggcggaca gagatgctct ggttaatgcc tggaaacatg ttgatgctca ggatatggcg     1620
aataaactgg gtaatctcag caaggctttt aaagtcgccg acgtggtgat gaaggttgag     1680
aaggtccggg agaagagcat tgagggggtat gaaaccggga actgggggcc gctgatgctg     1740
gaggtggaat cctgggtgct cagtggtata gcttcctctg ttgctctggg gatttttttcc     1800 gctacattag gagcatatgc cttatctctt ggagttcctg ctattgctgt tggtatcgcc     1860
ggtattctac tcgcagcagt tgttggtgcg ttaattgatg ataagtttgc agatgctttg     1920
aataatgaaa taatccgacc tgcacattaa gtttgattaa aaggcagtgt tactgccttt     1980 ttttttaataa tttaaatgca gtgactggtg tgaatagcgt gatataggtt gtaaagaaaa     2040
ttattgagta cagaccaata taaaataaca atagtgttgc gtcattggtg gccattaatc     2100
tgacaggcct tccggctgtt gtt                                              2123
```

<210> SEQ ID NO 15
<211> LENGTH: 600
<212> TYPE: PRT
<213> ORGANISM: Citrobacter freundii

<400> SEQUENCE: 15

```
Met His His His His His His His Pro Gly Phe Asn Tyr Gly Gly
1               5                   10                  15

Lys Gly Asp Gly Thr Gly Trp Ser Ser Glu Arg Gly Ser Gly Pro Glu
            20                  25                  30

Pro Gly Gly Gly Ser His Gly Asn Ser Gly Gly His Asp Arg Gly Asp
        35                  40                  45

Ser Ser Asn Val Gly Asn Glu Ser Val Thr Val Met Lys Pro Gly Asp
50                  55                  60

Ser Tyr Asn Thr Pro Trp Gly Lys Val Ile Ile Asn Ala Ala Gly Gln
65                  70                  75                  80

Pro Thr Met Asn Gly Thr Val Met Thr Ala Asp Asn Ser Ser Met Val
                85                  90                  95

Pro Tyr Gly Arg Gly Phe Thr Arg Val Leu Asn Ser Leu Val Asn Asn
            100                 105                 110

Pro Val Ser Pro Ala Gly Gln Asn Gly Gly Lys Ser Pro Val Gln Thr
        115                 120                 125

Ala Val Glu Asn Tyr Leu Met Val Gln Ser Gly Asn Leu Pro Pro Gly
130                 135                 140

Tyr Trp Leu Ser Asn Gly Lys Val Met Thr Glu Val Arg Glu Glu Arg
145                 150                 155                 160

Thr Ser Gly Gly Gly Lys Asn Gly Asn Glu Arg Thr Trp Thr Val
                165                 170                 175

Lys Val Pro Arg Glu Val Pro Gln Leu Thr Ala Ser Tyr Asn Glu Gly
            180                 185                 190

Met Arg Ile Arg Gln Glu Ala Ala Asp Arg Ala Arg Ala Glu Ala Asn
        195                 200                 205

Ala Arg Ala Leu Ala Glu Glu Ala Arg Ala Ile Ala Ser Gly Lys
210                 215                 220

Ser Lys Ala Glu Phe Asp Ala Gly Lys Arg Val Glu Ala Ala Gln Ala
225                 230                 235                 240

Ala Ile Asn Thr Ala Gln Leu Asn Val Asn Asn Leu Ser Gly Ala Val
                245                 250                 255

Ser Ala Ala Asn Gln Val Ile Thr Gln Lys Gln Ala Glu Met Thr Pro
            260                 265                 270

Leu Lys Asn Glu Leu Ala Ala Ala Asn Gln Arg Val Gln Glu Thr Leu
        275                 280                 285

Lys Phe Ile Asn Asp Pro Ile Arg Ser Arg Ile His Phe Asn Met Arg
290                 295                 300

Ser Gly Leu Ile Arg Ala Gln His Asn Val Asp Thr Lys Gln Asn Glu
305                 310                 315                 320

Ile Asn Ala Ala Val Ala Asn Arg Asp Ala Leu Asn Ser Gln Leu Ser
                325                 330                 335

Gln Ala Asn Asn Ile Leu Gln Asn Ala Arg Asn Glu Lys Ser Ala Ala
            340                 345                 350

Asp Ala Ala Leu Ser Ala Ala Thr Ala Gln Arg Leu Gln Ala Glu Ala
        355                 360                 365

Ala Leu Arg Ala Ala Ala Glu Ala Ala Lys Ala Arg Gln Arg Gln
370                 375                 380

Ala Glu Glu Ala Glu Arg Gln Arg Gln Ala Met Glu Val Ala Glu Lys
385                 390                 395                 400

Ala Lys Asp Glu Arg Glu Leu Leu Glu Lys Thr Ser Glu Leu Ile Ala
            405                 410                 415
```

```
Gly Met Gly Asp Lys Ile Gly Glu His Leu Gly Asp Lys Tyr Lys Ala
            420                 425                 430
Ile Ala Lys Asp Ile Ala Asp Asn Ile Lys Asn Phe Gln Gly Lys Thr
        435                 440                 445
Ile Arg Ser Phe Asp Asp Ala Met Ala Ser Leu Asn Lys Ile Thr Ala
    450                 455                 460
Asn Pro Ala Met Lys Ile Asn Lys Ala Asp Arg Asp Ala Leu Val Asn
465                 470                 475                 480
Ala Trp Lys His Val Asp Ala Gln Asp Met Ala Asn Lys Leu Gly Asn
                485                 490                 495
Leu Ser Lys Ala Phe Lys Val Ala Asp Val Val Met Lys Val Glu Lys
            500                 505                 510
Val Arg Glu Lys Ser Ile Glu Gly Tyr Glu Thr Gly Asn Trp Gly Pro
        515                 520                 525
Leu Met Leu Glu Val Glu Ser Trp Val Leu Ser Gly Ile Ala Ser Ser
    530                 535                 540
Val Ala Leu Gly Ile Phe Ser Ala Thr Leu Gly Ala Tyr Ala Leu Ser
545                 550                 555                 560
Leu Gly Val Pro Ala Ile Ala Val Gly Ile Gly Ile Leu Leu Ala
                565                 570                 575
Ala Val Val Gly Ala Leu Ile Asp Asp Lys Phe Ala Asp Ala Leu Asn
            580                 585                 590
Asn Glu Ile Ile Arg Pro Ala His
        595                 600

<210> SEQ ID NO 16
<211> LENGTH: 1803
<212> TYPE: DNA
<213> ORGANISM: Citrobacter freundii

<400> SEQUENCE: 16
atgcaccacc atcaccacca tcaccaccct ggatttaatt atggtggaaa aggtgatgga      60
accggctgga gctcagaacg tgggagtggt ccagagccgg tggtggtag ccatggaaat     120 agtggtgggc acgatcgtgg agattcttcc aacgtaggta atgagtctgt gacggtaatg     180
aaaccagggg attcgtataa cacccccgtgg ggaaaagtca tcatcaatgc tgcaggccag     240
ccgaccatga acggaacggt gatgaccgct gataattcat cgatggttcc ttacggcaga     300
gggtttacac gggttttaaa ttccctggtc aataatcctg tttcgccggc aggtcagaat     360
ggcgggaagt ctcctgttca gactgctgtg gaaaattatc tgatggtaca gtcaggaaac     420
ctgccaccgg gctactggct cagtaatggc aaggttatga cggaggttcg tgaggaacgt     480
acttctggcg gcgtgggaa aaacgggaac gagcgaacct ggactgtgaa agttccccgg     540
gaagtacctc agcttacggc atcctataac gaggggatga gaatccgaca ggaggcagct     600
gaccgtgcca gagcggaagc aaatgcccgc gctctggctg aagaggaagc ccgtgccatc     660
gcatcaggaa agagcaaagc tgagtttgat gcaggtaagc gggtggaggc cgcacaggca     720
gcgattaata cagcacaact caatgttaat aacctcagcg cgctgtcag tgctgcaaat     780 caggttataa ctcagaaaca ggctgaaatg acgcccctga aaaatgagct tgcagccgct     840
aaccagcgtg tccaggagac gcttaaattt atcaatgatc ctattcgtag ccggattcat     900
tttaatatgc gaagtggcct gattcgcgct caacataacg ttgatactaa acagaatgaa     960
attaatgcag cagtggctaa ccgtgatgct ctgaatagcc aattgtctca ggctaataat    1020
atcctgcaga atgcccggaa cgaaaagagt gcggctgatg cagcactttc agctgccaca    1080
```

-continued

```
gcacagcggt tacaggcaga agccgcactc agggctgctg ctgaggctgc agaaaaagcg    1140
cgccagcgcc aggctgaaga agccgaacgt cagcgtcagg ctatggaagt tgcggaaaaa    1200
gccaaagatg agcgggagct gcttgaaaaa accagtgaac tgattgctgg tatgggagat    1260
aaaatcggcg agcatcttgg agataaatat aaggcgatag cgaaagatat tgcggacaat    1320
attaaaaatt ttcaggggaa gaccatccgt agctttgatg atgcaatggc atcgctgaat    1380
aaaatcacag ccaacccagc catgaaaatt aataaggcgg acagagatgc tctggttaat    1440
gcctggaaac atgttgatgc tcaggatatg gcgaataaac tgggtaatct cagcaaggct    1500
tttaaagtcg ccgacgtggt gatgaaggtt gagaaggtcc gggagaagag cattgagggg    1560
tatgaaaccg ggaactgggg gccgctgatg ctggaggtgg aatcctgggt gctcagtggt    1620
atagcttcct ctgttgctct ggggattttt tccgctacat taggagcata tgccttatct    1680
cttggagttc ctgctattgc tgttggtatc gccggtattc tactcgcagc agttgttggt    1740
gcgttaattg atgataagtt tgcagatgct ttgaataatg aaataatccg acctgcacat    1800
taa                                                                  1803
```

<210> SEQ ID NO 17
<211> LENGTH: 599
<212> TYPE: PRT
<213> ORGANISM: Citrobacter freundii

<400> SEQUENCE: 17

```
Met Pro Gly Phe Asn Tyr Gly Gly Lys Gly Asp Gly Thr Gly Trp Ser
1               5                   10                  15

Ser Glu Arg Gly Ser Gly Pro Glu Pro Gly Gly Gly Ser His Gly Asn
            20                  25                  30

Ser Gly Gly His Asp Arg Gly Asp Ser Ser Asn Val Gly Asn Glu Ser
        35                  40                  45

Val Thr Val Met Lys Pro Gly Asp Ser Tyr Asn Thr Pro Trp Gly Lys
    50                  55                  60

Val Ile Ile Asn Ala Ala Gly Gln Pro Thr Met Asn Gly Thr Val Met
65                  70                  75                  80

Thr Ala Asp Asn Ser Ser Met Val Pro Tyr Gly Arg Gly Phe Thr Arg
                85                  90                  95

Val Leu Asn Ser Leu Val Asn Asn Pro Val Ser Pro Ala Gly Gln Asn
            100                 105                 110

Gly Gly Lys Ser Pro Val Gln Thr Ala Val Glu Asn Tyr Leu Met Val
        115                 120                 125

Gln Ser Gly Asn Leu Pro Pro Gly Tyr Trp Leu Ser Asn Gly Lys Val
    130                 135                 140

Met Thr Glu Val Arg Glu Arg Thr Ser Gly Gly Gly Lys Asn
145                 150                 155                 160

Gly Asn Glu Arg Thr Trp Thr Val Lys Val Pro Arg Glu Val Pro Gln
                165                 170                 175

Leu Thr Ala Ser Tyr Asn Gly Met Arg Ile Arg Gln Glu Ala Ala
            180                 185                 190

Asp Arg Ala Arg Ala Glu Ala Asn Ala Arg Ala Leu Ala Glu Glu Glu
        195                 200                 205

Ala Arg Ala Ile Ala Ser Gly Lys Ser Lys Ala Glu Phe Asp Ala Gly
    210                 215                 220
```

Lys Arg Val Glu Ala Ala Gln Ala Ala Ile Asn Thr Ala Gln Leu Asn
225                 230                 235                 240

Val Asn Asn Leu Ser Gly Ala Val Ser Ala Ala Asn Gln Val Ile Thr
            245                 250                 255

Gln Lys Gln Ala Glu Met Thr Pro Leu Lys Asn Glu Leu Ala Ala Ala
        260                 265                 270

Asn Gln Arg Val Gln Glu Thr Leu Lys Phe Ile Asn Asp Pro Ile Arg
    275                 280                 285

Ser Arg Ile His Phe Asn Met Arg Ser Gly Leu Ile Arg Ala Gln His
290                 295                 300

Asn Val Asp Thr Lys Gln Asn Glu Ile Asn Ala Ala Val Ala Asn Arg
305                 310                 315                 320

Asp Ala Leu Asn Ser Gln Leu Ser Gln Ala Asn Asn Ile Leu Gln Asn
            325                 330                 335

Ala Arg Asn Glu Lys Ser Ala Ala Asp Ala Ala Leu Ser Ala Ala Thr
        340                 345                 350

Ala Gln Arg Leu Gln Ala Glu Ala Ala Leu Arg Ala Ala Ala Glu Ala
    355                 360                 365

Ala Glu Lys Ala Arg Gln Arg Gln Ala Glu Glu Ala Glu Arg Gln Arg
370                 375                 380

Gln Ala Met Glu Val Ala Glu Lys Ala Lys Asp Glu Arg Glu Leu Leu
385                 390                 395                 400

Glu Lys Thr Ser Glu Leu Ile Ala Gly Met Gly Asp Lys Ile Gly Glu
            405                 410                 415

His Leu Gly Asp Lys Tyr Lys Ala Ile Ala Lys Asp Ile Ala Asp Asn
        420                 425                 430

Ile Lys Asn Phe Gln Gly Lys Thr Ile Arg Ser Phe Asp Asp Ala Met
    435                 440                 445

Ala Ser Leu Asn Lys Ile Thr Ala Asn Pro Ala Met Lys Ile Asn Lys
450                 455                 460

Ala Asp Arg Asp Ala Leu Val Asn Ala Trp Lys His Val Asp Ala Gln
465                 470                 475                 480

Asp Met Ala Asn Lys Leu Gly Asn Leu Ser Lys Ala Phe Lys Val Ala
            485                 490                 495

Asp Val Val Met Lys Val Glu Lys Val Arg Glu Lys Ser Ile Glu Gly
        500                 505                 510

Tyr Glu Thr Gly Asn Trp Gly Pro Leu Met Leu Glu Val Glu Ser Trp
    515                 520                 525

Val Leu Ser Gly Ile Ala Ser Ser Val Ala Leu Gly Ile Phe Ser Ala
530                 535                 540

Thr Leu Gly Ala Tyr Ala Leu Ser Leu Gly Val Pro Ala Ile Ala Val
545                 550                 555                 560

Gly Ile Ala Gly Ile Leu Leu Ala Ala Val Val Gly Ala Leu Ile Asp
            565                 570                 575

Asp Lys Phe Ala Asp Ala Leu Asn Asn Glu Ile Ile Arg Pro Ala His
        580                 585                 590

His His His His His His
        595

<210> SEQ ID NO 18
<211> LENGTH: 1800
<212> TYPE: DNA
<213> ORGANISM: Citrobacter freundii -continued

```
<400> SEQUENCE: 18
atgcctggat ttaattatgg tggaaaaggt gatggaaccg gctggagctc agaacgtggg      60
agtggtccag agccgggtgg tggtagccat ggaaatagtg gtgggcacga tcgtggagat     120
tcttccaacg taggtaatga gtctgtgacg gtaatgaaac caggggattc gtataacacc     180
ccgtggggaa aagtcatcat caatgctgca ggccagccga ccatgaacgg aacggtgatg     240
accgctgata attcatcgat ggttccttac ggcagagggt ttacacgggt tttaaattcc     300
ctggtcaata atcctgtttc gccggcaggt cagaatggcg ggaagtctcc tgttcagact     360
gctgtggaaa attatctgat ggtacagtca ggaaacctgc caccgggcta ctggctcagt     420
aatggcaagg ttatgacgga ggttcgtgag gaacgtactt ctggcggcgg tgggaaaaac     480
gggaacgagc gaacctggac tgtgaaagtt ccccgggaag tacctcagct tacggcatcc     540
tataacgagg ggatgagaat ccgacaggag gcagctgacc gtgccagagc ggaagcaaat     600
gcccgcgctc tggctgaaga ggaagcccgt gccatcgcat caggaaagag caaagctgag     660
tttgatgcag gtaagcgggt ggaggccgca caggcagcga ttaatacagc acaactcaat     720
gttaataacc tcagcggcgc tgtcagtgct gcaaatcagg ttataactca gaaacaggct     780
gaaatgacgc ccctgaaaaa tgagcttgca gccgctaacc agcgtgtcca ggagacgctt     840
aaatttatca atgatcctat tcgtagccgg attcatttta atatgcgaag tggcctgatt     900
cgcgctcaac ataacgttga tactaaacag aatgaaatta atgcagcagt ggctaaccgt     960
gatgctctga atagccaatt gtctcaggct aataatatcc tgcagaatgc ccggaacgaa    1020
aagagtgcgg ctgatgcagc actttcagct gccacagcac agcggttaca ggcagaagcc    1080
gcactcaggg ctgctgctga ggctgcagaa aaagcgcgcc agcgccaggc tgaagaagcc    1140
gaacgtcagc gtcaggctat ggaagttgcg gaaaaagcca aagatgagcg ggagctgctt    1200
gaaaaaacca gtgaactgat tgctggtatg ggagataaaa tcggcgagca tcttggagat    1260
aaatataagg cgatagcgaa agatattgcg gacaatatta aaaattttca ggggaagacc    1320
atccgtagct ttgatgatgc aatggcatcg ctgaataaaa tcacagccaa cccagccatg    1380
aaaattaata aggcggacag agatgctctg gttaatgcct ggaaacatgt tgatgctcag    1440
gatatggcga ataaactggg taatctcagc aaggctttta aagtcgccga cgtggtgatg    1500
aaggttgaga aggtccggga gaagagcatt gaggggtatg aaaccgggaa ctgggggccg    1560
ctgatgctgg aggtggaatc ctgggtgctc agtggtatag cttcctctgt tgctctgggg    1620 atttttccg ctacattagg agcatatgcc ttatctcttg gagttcctgc tattgctgtt    1680
ggtatcgccg gtattctact cgcagcagtt gttggtgcgt taattgatga taagtttgca    1740
gatgctttga ataatgaaat aatccgacct gcacatcacc accatcacca ccatcactaa    1800
```

CITROBACTER FREUNDII ANTIBACTERIAL AGENTS AND THEIR USE

CROSS REFERENCE TO RELATED APPLICATION

This application claims the benefit of U.S. Provisional Application No. 61/499,675, filed Jun. 21, 2011, which is incorporated herein by reference.

ACKNOWLEDGMENT OF GOVERNMENT SUPPORT

This invention was made with government support under NIH grant number AI085570 awarded by the Department of Health and Human Services. The government has certain rights in the invention.

FIELD

This disclosure relates generally to antimicrobial agents and methods for their use.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Jun. 15, 2012, and having a size of ~32.6 kilobytes, as permitted under 37 CFR 1.821(c). The material in the aforementioned file is hereby incorporated by reference in its entirety.

BACKGROUND

Members of the Enterobacteriaciae family of Gram-negative bacteria are among the most common food-borne and hospital acquired pathogens. These organisms have had a huge impact upon human history by causing devastating diseases, such as the black plague and typhoid fever, as well as more common urinary tract infections, dysentery and hospital acquired infections. Many members of the Enterobacteriaciae are well known for acquiring antibiotic resistance, including pan-resistant strains of *Klebsiella pneumoniae*, and carbapenem-resistant *Escherichia coli* and *Serratia marcescens*. The discovery of the ndm-1 carbapenemase has underscored the need to identify novel antibiotics.

Bacteria can gain resistance through acquisition of additional DNA from a plasmid or other source, mutation of an antibiotic target site or a transporter protein, or other genetic mechanism. However, most bacteria can also gain antibiotic tolerance through formation of a biofilm. Cells in a biofilm are up to 1000 times more tolerant to antibiotics and disinfectants compared to their planktonic counterparts. Thus, deleterious biofilms cause serious problems such as chronic infections in humans, as well as persistent corrosion and equipment failure in industry. Although mechanisms by which bacteria in biofilms resist killing by antibiotics are not completely elucidated, several mechanisms have been postulated. *Pseudomonas aeruginosa* has two different active mechanisms by which biofilms gain antibiotic tolerance. In one of these, periplasmic cyclic glucans are produced in biofilm cells that bind to aminoglycosides. Another mechanism is the modification of the lipid A component of lipopolysaccharide in response to extracellular DNA found in a biofilm, resulting in diminished activity of antimicrobial peptides. In both of these examples, differential gene expression in the biofilm leads to reduced antibiotic susceptibility. Other mechanisms by which biofilms resist antibiotic activity include the presence of "persister" cells, microenvironments within the biofilm that prevent the antibiotic from working, and inhibition of antibiotic access to bacteria within a biofilm. There is therefore a continued need for new antibiotics, particularly antibiotics that are effective against established biofilms.

SUMMARY

Multi- and pan-antibiotic resistant bacteria are a major health challenge, particularly in hospital settings. When bacteria that are susceptible or sensitive to antibacterial agents establish surface attached biofilm populations, they become less sensitive (or resistant) to antimicrobial therapy. Therefore there is an urgent need for novel antibacterial agents that are effective against multi-drug resistant planktonic bacteria and/or biofilms that contain surface attached bacteria.

Thus, provided herein are methods for treating planktonic bacteria or a biofilm, for example by inhibiting the formation, growth, or maintenance of the bacteria or biofilm. The methods include contacting the planktonic bacteria or biofilm with an effective amount of an isolated *Citrobacter freundii* colicin A polypeptide, wherein the polypeptide has an antibacterial activity against the planktonic bacteria or the biofilm. The methods can be used to treat a biofilm on a living or non-living surface. An example of a non-living surface is a surface of a medical device that is suitable for surgical implantation within a subject.

Methods are also provided herein for treating a subject that has a bacterial infection, for example a chronic infection caused by a biofilm. The method includes administering to the subject a therapeutically effective amount of a pharmaceutical composition comprising a *Citrobacter freundii* colicin A polypeptide, wherein the polypeptide has an antibacterial activity against the biofilm. In one embodiment, the biofilm is on a medical device implanted in the subject. In other embodiments, the *Citrobacter freundii* colicin A polypeptide is provided on a medical device, such as an implantable medical device, to inhibit formation and/or growth of the biofilm on the medical device. Also disclosed is such a medical device which comprises the polypeptide on a surface of the device, particularly on a surface that will be susceptible to formation of a biofilm when the device is implanted in a subject.

The disclosed *Citrobacter freundii* colicin A polypeptides have an antibacterial activity against planktonic bacteria or surface attached bacteria, for example surface attached bacteria in an established biofilm. Thus, the *Citrobacter freundii* colicin A polypeptides can inhibit the growth or proliferation of planktonic bacteria or a biofilm. An example of a *Citrobacter freundii* colicin A polypeptide is the amino acid sequence set forth as SEQ ID NO: 1. An example of an isolated nucleic acid molecule which encodes the isolated *Citrobacter freundii* polypeptide is the nucleic acid sequence set forth as SEQ ID NO: 2.

The foregoing and other objects, features, and advantages of the invention will become more apparent from the following detailed description, which proceeds with reference to the accompanying figures.

BRIEF DESCRIPTION OF THE DRAWINGS

FIGS. 1A, 1B, and 1C are a series of digital images showing the identification of an antimicrobial compound from *C. freundii* ATCC 43864. FIG. 1A demonstrates the results of a microbial inhibition assay. *C. freundii* ATCC 43864 was grown in liquid broth for 24 hrs, cells (I) or filter-sterilized supernatant (II) and were spotted on a lawn of sensitive *C. freundii* NCTC 9750. Antimicrobial activity was seen by the formation of a zone of inhibition around or at the point of inoculation. FIG. 1B demonstrates the screening for *C. freundii* ATCC 43864 mutants defective in the production of the antimicrobial compound. *C. freundii* ATCC 43864 transposon mutants were grown in a 96 well microtiter dish. Aliquots were transferred onto a lawn of sensitive *C. freundii* NCTC 9750. The plates were then incubated at 37° C. and examined for the formation of a zone of clearing where the mutants were spotted. The arrow indicates the location of mutants impaired in their ability to produce antimicrobial compound. FIG. 1C demonstrates the results of the microbial inhibition assay of a *C. freundii* ATCC 43864 antimicrobial defective mutant. *C. freundii* ATCC 43864 wild-type and Cf-8A were grown in liquid broth for 24 hours, cells (I) or filter-sterilized supernatant (II) were spotted on a lawn of sensitive *C. freundii* NCTC 9750. Antimicrobial activity was seen by the formation of a zone of inhibition around or at the point of inoculation.

FIG. 4A demonstrates the purification fractions of CfbX-His$_8$ analyzed by polyacrylamide gel electrophoresis (PAGE). Crude lysates with empty vector negative control (pMQ124) or pMQ124+ His$_8$-cfbX-his$_8$ (pMQ348) were generated identically and purified by Immobilized Metal Ion Affinity Chromatography (IMAC). Fractions for crude fraction (C), column flow-through (F), wash (W), and elution (E), and the size standard (L) are shown. FIG. 4B is an immunoblot analysis of each fraction probed with an anti-poly-histidine antibody. Immunoblot lanes are aligned with those of the PAGE in FIG. 4A.

FIG. 6A demonstrates the effect of CfbX on planktonic bacteria. Tested bacteria (~$10^9$ CFU/ml) were incubated for 30 minutes with PBS (black bars) 87 µg protein extracted from empty vector control *E. coli* S17-pMQ124 (white bars) and 37 µg protein isolated from *E. coli* S17-pMQ348 (grey bars). Cell viability was measured at time 0 and following the 30 minute incubation. Each value represents the mean of 3 experiments. Error bars are shown as one-standard deviation. FIG. 6B demonstrates the effect of CfbX on biofilms. Overnight biofilms (composed of ~$10^6$-$10^7$ CFU/ml) were incubated for 120 minutes with PBS (black bars) and 175 µg protein extracted from empty vector control *E. coli* S17-pMQ124 (white bars). Biofilms were also incubated, for 30 minutes (grey bars) and 120 minutes (striped grey bars), with 75 µg protein isolated from *E. coli* S17-pMQ348. Cell viability was measured at time 0 and following incubation. Each value represents the mean of 3 experiments. Error bars are shown as one-standard deviation. FIG. 6C is a series of CLSM micrographs demonstrating the effect of CfbX on biofilms. Overnight biofilms of *C. freundii* ATCC 8090 were incubated for 60 minutes with protein (11.6 µg/ml final concentration) extracted from empty vector control *E. coli* S17-pMQ124 or the colicin bearing plasmid *E. coli* S17-pMQ348. Thereafter the biofilms were stained with Syto-9 (to identify live cells) and propidium iodide (to identify dead cells). A representative image is shown. Images were taken at the same exposures with a 40× magnification objective.

FIG. 7A demonstrates the effect of IMAC-purified CfbX on planktonic bacteria. FIG. 7B demonstrates the effect of IMAC-purified CfbX on biofilm bacteria. *C. freundii* NCTC 9750 ($6 \times 10^9$ and $2 \times 10^6$ CFU/ml for planktonic and biofilm, respectively) were incubated, for 30 minutes, in the presence of 2.0-0.02 µg IMAC-purified CfbX, PBS control and mock IMAC-purified sample from *E. coli* S17-pMQ124. Cell viability was measured at time 0 and following incubation. Each value represents the mean of 3 experiments. Error bars are shown as one-standard deviation.

FIG. 8A demonstrates the results of a bacteriocin antimicrobial activity assay. Crude bacteriocin extracts were spotted on microbial lawns of *C. freundii* NCTC 9750 and *C. freundii* ATCC 8090, and *E. coli* S17-1, as well as transformants harboring plasmids: pMQ124 (empty vector) pCfc1-8A (cfbX defective, intact immunity gene) or pRMQS345 (vector+bacteriocin immune gene). Antimicrobial activity is seen by the formation of a zone of inhibition were the bacteriocin was spotted. FIG. 8B demonstrates the effect of bacteriocin on *E. coli* harboring the immune gene. Planktonically grown *E. coli* S17-pRMQS345 and an empty vector control *E. coli* S17-pMQ124 (~$10^7$ CFU/ml) were incubated for 30 minutes with PBS (black bars), 87 µg protein extracted from empty vector control *E. coli* S17-pMQ124 (white bars), and 37 µg protein derived from *E. coli* S17-pMQ348 (grey bars). Cell viability was measured at time 0 and following incubation. Each value represents the mean of 3 experiments. Error bars are shown as one-standard deviation.

SEQUENCE LISTING

Figure 2:
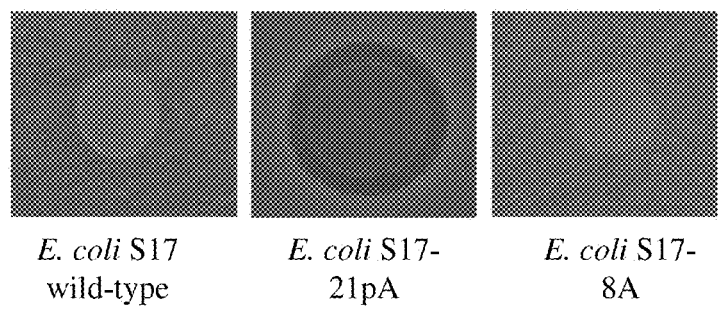
FIG. 2 is a series of digital images showing the transformation of *E. coli* with pCfc1. Overnight cultures of wild-type *E. coli* S17-1, *E. coli* S17-21pA and *E. coli*-8A were spotted on a lawn of sensitive *C. freundii* NCTC 9750. Antimicrobial activity was seen by the formation of a zone of inhibition around the point of inoculation. The *E. coli*-8A strain has a mutation in the colicin A gene (cfbX).

The nucleic and amino acid sequences listed herein and/or herewith are shown using standard letter abbreviations for nucleotide bases, and three letter code for amino acids, as defined in 37 C.F.R. §1.822. Only one strand of each nucleic acid sequence is shown, but the complementary strand is understood as included by any reference to the displayed strand.

SEQ ID NO: 1 shows the amino acid sequence of the *Citrobacter freundii* ATCC 43864 CfbX protein.

SEQ ID NO: 2 shows the nucleic acid sequence of the *Citrobacter freundii* ATCC 43864 cfbX coding sequence.

SEQ ID NOs: 3-12 are primers

SEQ ID NO: 13 shows the amino acid sequence of the *Citrobacter freundii* strain CA31 colA protein.

SEQ ID NO: 14 shows the nucleic acid sequence of the *Citrobacter freundii* strain CA31 colA gene. Residues 172 to 1950 of SEQ ID NO: 14 encode the CA31 colA protein.

SEQ ID NO: 15 shows the amino acid sequence of the amino terminal poly-histidine tagged *Citrobacter freundii* ATCC 43864 CfbX protein.

SEQ ID NO: 16 shows the nucleic acid sequence of the amino terminal poly-histidine tagged *Citrobacter freundii* ATCC 43864 cfbX coding sequence.

SEQ ID NO: 17 shows the amino acid sequence of the carboxy terminal poly-histidine tagged *Citrobacter freundii* ATCC 43864 CfbX protein.

SEQ ID NO: 18 shows the nucleic acid sequence of the carboxy terminal poly-histidine tagged *Citrobacter freundii* ATCC 43864 cfbX coding sequence.

DETAILED DESCRIPTION

I. Abbreviations

| ATCC | American Type Culture Collection |
|---|---|
| BSA | Bovine serum albuim |
| CfbX | *Citrobacter freundii* anti-biofilm factor x |
| CFU | Colony forming unit |
| CLSM | Confocal laser scanning microscope |
| DAP | Diaminopimelic acid |
| Gm$^r$ | Gentamicin-resistant |
| HRP | Horseradish peroxidase |
| IMAC | Immobilized Metal Ion affinity Chromatography |
| LB | Lysogeny Broth |
| LPS | Lipopolysaccharide |
| NEB | New England Biolabs |
| PAGE | Polyacrylamide gel electrophoresis |
| PBS | Phosphate buffered saline |
| PCR | Polymerase chain reaction |
| v/v | Volume/volume |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects, for example, non-human primates, dogs, cats, horses, rabbits, pigs, mice, rats, and cows.

Antibacterial agent: An agent that kills bacteria, or suppresses (or inhibits) their growth or multiplication. The bacteria can be planktonic or surface attached, for example surface attached bacteria in a biofilm. An antibacterial agent includes, but is not limited to, a chemical compound, a small molecule, a peptide mimetic, a peptide, a protein, or a bacteriophage for killing microorganisms or suppressing their multiplication, proliferation, or growth. In some specific embodiments, an antibacterial agent is a bacteriocin, an antimicrobial peptide, an antibiotic, or a bacteriophage.

In one embodiment, antibacterial activity can be measured by the production or the size (i.e. diameter of) of a clear zone surrounding a bacterial colony on a bacterial lawn, wherein the antibacterial agent is produced, secreted, or expressed by the bacteria in the bacterial colony. In another embodiment, an antibacterial activity is measured by bacterial cell lysis. In a further embodiment, an antibacterial activity is measured by a reduction in bacterial cell viability, for example a reduction in bacterial cell viability in a lawn of bacteria or in a biofilm. A specific, non-limiting example of an agent with antibacterial activity includes, but is not limited to, a *Citrobacter freundii* colicin A polypeptide, for example a CfbX polypeptide.

Antibacterial enzyme: An enzyme (such as a proteolytic, pore-forming, degradative, or inhibitory enzyme) that kills or damages a bacterial species or particular strain thereof. The enzyme can damage the cell wall of the bacteria, disrupt cell membranes associated with the cell wall or within the bacteria, inhibit protein synthesis within the bacteria, or disrupt the sugar backbone. The enzyme may be a natural, wild-type enzyme, a variant modified by conventional techniques, conjugated to other molecules, recombinantly expressed, or synthetically constructed.

Examples of antibacterial enzymes include, but are not limited to, a lytic enzyme, an acylase, an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, and lysostaphin.

Antibiotic: A chemical substance, such as one produced by microorganisms, that kills bacteria (bactericidal) and/or inhibits the growth, proliferation, or multiplication of bacteria (bacteriostatic). Exemplary antibacterial antibiotics include, but are not limited to, a beta-lactam, a cephalosporin, an aminoglycoside, a sulfonamide, a macrolide, a tetracycline, a silver salt, and the like.

Antimicrobial agent: An agent that kills microorganisms or suppresses (or inhibits) their growth, proliferation, or multiplication. An antimicrobial agent includes, but is not limited to, a chemical compound, a small molecule, a peptide mimetic, a peptide, a protein, or a bacteriophage for killing microorganisms or suppressing their proliferation, multiplication or growth. In some specific embodiments, an antimicrobial agent is an antibacterial agent, an antifungal agent, or an antiprotozoal agent.

An agent has "antimicrobial activity" if it can interfere with a microorganism in such a way that it results in the death of a microorganism or suppresses the growth, proliferation, or multiplication of a microorganism. An antimicrobial activity includes, but is not limited to, microbial cell lysis. In one embodiment, an antimicrobial agent is cytotoxic. An antimicrobial agent includes both microbiocidal agents (agents that kill a microorganism), as well as those agents that inhibit growth or maintain stasis of target microorganisms. In particular embodiments, an antimicrobial agent is an antibacterial agent (targets bacteria), an antiprotozoal agent (targets protozoa), or an antifungal agent (targets fungi). In another embodiment, antimicrobial activity can be measured by the production or the size (i.e. diameter) of a clear zone surrounding a bacterial colony on a microbial lawn, wherein the antimicrobial agent is produced, secreted, or expressed by the bacteria in the bacterial colony. In one embodiment, an antimicrobial activity is measured by bacterial cell lysis (an antibacterial activity). In a further embodiment, an antimicrobial activity is measured by a reduction in bacterial cell viability, for example a reduction in bacterial cell viability in a biofilm. In other embodiments, an antimicrobial activity is measured by fungal lysis (antifungal activity) or protozoan lysis (antiprotozoal activity). A specific, non-limiting example of an agent with antimicrobial activity includes, but is not limited to, a *Citrobacter freundii* colicin A polypeptide, for example a CfbX polypeptide.

Bacteriocin: A toxic protein produced by a given strain of bacteria and active against related species of bacteria, but not against the producing bacterial cells.

Bioassay: Measurement of the concentration or potency of a substance by its effect on living cells or tissues.

Biofilm: A mass, aggregation, or community of microorganisms attached to a living surface (such as a surface of a tissue or an organ) or a non-living surface (such as a surface of a medical device, a household surface, a food preparation object, or a fluid-conducting device having a lumen, such as a pipe, tubing, or a catheter), and the associated extracellular substances produced by one or more of the attached microorganisms. The extracellular substances are typically polymeric substances that include a matrix of complex polysaccharides, proteinaceous substances, nucleic acids, and glycopeptides. The microorganisms in a biofilm may include, but are not limited to, bacteria, fungi and protozoa. In a "bacterial biofilm," the microorganisms include one or more species of bacteria. The nature of a biofilm, such as its structure and composition, may depend on the particular species of bacteria present in the biofilm.

Bacteria present in a biofilm are generally genetically identical to their planktonic counterparts. However, in some embodiments, the presence of specific genetic determinants within one strain of a species of bacteria can confer a propensity or greater ability in that strain of bacteria to form biofilms. Bacteria present in a biofilm may be phenotypically different than their planktonic counterparts. For example, bacteria in biofilms are commonly (i) more highly resistant (for example, 1000× more resistant) to antimicrobial agents and biocides than genetically identical planktonic bacteria; (ii) more highly resistant to phagocytosis, antibodies, and other immune system components than genetically identical planktonic bacteria; and (iii) have differential gene expression patterns, compared to planktonic bacteria. "Polymicrobic biofilms" are biofilms that include a plurality of bacterial species. In one embodiment, a biofilm is recalcitrant (or resistant) to antimicrobial or antibacterial treatments that are normally effective at inhibiting or controlling the growth of the corresponding planktonic bacteria. In one embodiment, the cells of a biofilm that are recalcitrant or resistant to antimicrobial or antibacterial treatments are persister cells.

*Citrobacter freundii*: A Gram-negative bacteria of the Enterobacteriaceae family responsible for opportunistic infections, as well as nosocomial (hospital derived) infections of the respiratory tract, urinary tract, blood, and several other normally sterile sites in patients. *Citrobacter freundii* usually utilize citrate as a sole carbon source. These facultative anaerobes typically are motile by means of peritrichous flagella. In addition, they ferment glucose and other carbohydrates with the productions of acid and gas. They are oxidase negative, catalase and methyl red positive, Voges-Proskauer negative, and do not decarboxylate lysine. *Citrobacter freundii* species are differentiated by their ability to convert tryptophan to indole, ferment lactose, and use malonate. *Citrobacter freundii* can be found in water, feces, and urine.

Colicin: A secreted, antibiotic protein (a bacteriocin) produced by strains of Enterobacteriaceae which carry specific plasmids called colicinogenic factors. In some embodiments, colonies of colicinogenic strains secrete colicin and cause a zone of growth-inhibition on a lawn of colicin-sensitive cells. Colicins have an effect on a narrow range of bacteria due to the presence of specific receptors to which colicin binds at the surface of the sensitive bacterial strains. Mutations in the cell-surface receptor can lead to the loss of sensitivity of the bacterial cell to the corresponding colicin. An alphabetic letter is used to designate the receptor to which colicin binds, and when more than one colicin binds to the same receptor, the colicins are designated by that letter followed by a number. For example, the nine E colicins are designated E1 to E9. The receptors are bacterial outer membrane proteins that allow the entry of specific nutrients such as nucleosides, siderophores, and vitamins into the organism.

Colicins are divided into two groups. Group A colicins include colicin A, E1, E2, E3, E4, E5, E6, E7, E8, E9, K, N, bacteriocin 28b, and cloacin DF13. Group B colicins include colicin B, D, Ia, Ib, M, V, 5, and 10. Structurally, colicins have three distinct domains: (i) a domain involved in the recognition of a specific receptor. (ii) a domain involved in translocation, and (iii) a domain responsible for the lethal activity (cytotoxic domain). In one particular embodiment, the amino ($NH_2$)-terminal region of colicin A (residues 1 to 172) is involved in translocating the *Citrobacter freundii* antibacterial agent through the outer membrane of a susceptible bacterial cell, the central region of colicin A (residues 173 to 336) contains the cell surface receptor-binding domain, and the carboxy (COOH)-terminal domain (residues 389 to 592) carries the pore-forming activity of the *Citrobacter freundii* antibacterial agent (Frenette et al., *Biochemistry*, 28(6): 2509-2514, 1989).

The cytotoxicity induced by colicins occurs as a result of (i) a pore-forming activity in the cytoplasmic membrane of the susceptible bacteria (e.g. colicins A, B, E1 or N); (ii) a non-specific DNase activity that belongs to the H—N—H family of homing endonucleases and shows homology to DNases responsible for eucaryotic apoptosis (e.g. colicins E2, E7, E8 or E9); (iii) a 16S RNase activity (e.g. colicins E3, E4, E6 and cloacin DF13); or (iv) an anticodon tRNase activity (e.g. colicin E5).

Colicin E2-E9 producing strains protect themselves against killing by producing a plasmid-encoded, immunity protein that forms a complex with its cognate cytotoxic domain upon synthesis, for example the ColE9/Im9 complex. To facilitate import of their cytotoxic domains to their cellular site of action, group A colicins, such as the E colicins and colicin A (ColA), use the tol-dependent translocation system that consists of the TolQ, TolR, TolA, TolB and Pal proteins, and constitutes a transmembrane protein translocation portal or translocon.

Effective amount: The "effective amount" of a composition is the quantity of a composition sufficient to achieve a desired result. For instance, this can be the amount of a composition containing a sufficient dose of an antimicrobial agent (an antimicrobial effective amount), such as a *Citrobacter freundii* polypeptide (for example, SEQ ID NO: 1 or a variant thereof), sufficient to inhibit the formation of a biofilm (for example, a bacterial biofilm) on a non-living or living surface, to treat an existing (established) biofilm on a non-living or living surface, or to treat an infection caused by planktonic bacteria. The effective amount of a composition will depend on, for example, the antimicrobial agent contained in the composition, the concentration of the antimicrobial agent in the composition, the amount of time the composition is in contact with the surface (or the biofilm or the cells), the temperature at which the interaction between the composition and the surface takes place, and the like.

Gram-negative bacteria: Bacteria that do not retain crystal violet dye in the Gram staining protocol, but take up the counterstain and appear red or pink.

Gram-positive bacteria: Bacteria that are stained dark blue or violet by Gram staining (i.e. the bacteria retain the crystal violet dye).

Indwelling medical device: A device introduced, inserted, or implanted into a subject for use in the body, such as intravascular catheters (for example, intravenous and intra-arterial), right heart flow-directed catheters, Hickman catheters, arteriovenous fistulae, catheters used in hemodialysis and peritoneal dialysis (for example, silastic, central venous, Tenckhoff, and Teflon catheters), vascular access ports, indwelling urinary catheters, urinary catheters, silicone catheters, ventricular catheters, synthetic vascular prostheses (for example, aortofemoral and femoropopliteal), prosthetic heart valves, prosthetic joints, orthopedic implants, penile implants, shunts (for example, Scribner, Torkildsen, central nervous system, portasystemic, ventricular, ventriculoperitoneal), intrauterine devices, dental implants, stents (for example, ureteral stents), artificial voice prostheses, tympanostomy tubes, gastric feeding tubes, endotracheal tubes, pacemakers, implantable defibrillators, tubing, cannulas, probes, blood monitoring devices, needles, mouth guards, night guards, dentures, orthodontic retainers, contact lenses, and the like. The indwelling medical device can be wholly embedded in the subject (for example, a prosthetic joint, a prosthetic heart valve, or a pacemaker). In some embodiments, the indwelling medical device is partially embedded in the subject and has both internal and external parts, relative to the subject (for example, a urinary catheter, a gastric feeding tube, or a dental implant).

In some embodiments, an indwelling device is surgically implanted (for example, a pacemaker, dental implants, prosthetic joints, vascular prostheses, or shunts). In other embodiments, an indwelling medical device is inserted into the subject by a medical professional using non-surgical means (for example, an intrauterine device, an endotracheal tube, or a urinary catheter). In yet other embodiments, an indwelling medical device includes devices that are routinely inserted and removed by the subject (for example, an inserted medical device) without intervention or aide by a medical professional (for example, a mouth guard, a night guard, removable dentures, an orthodontic retainer, or a contact lens).

Indwelling medical devices can be introduced by any suitable means, for example, by percutaneous, intra-vascular, intra-urethral, intra-orbital, intra-oral, intra-tracheal, intra-esophageal, stomal, or other route, or by surgical implantation, for example intra-articular placement of a prosthetic joint.

Isolated: An "isolated" biological component, such as a nucleic acid, protein or organelle that has been substantially separated or purified away from other biological components in the environment (such as a cell) in which the component naturally occurs, i.e., chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, nitorimidazoles, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the label is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ. In other embodiments, the label is a protein tag recognized by an antibody, for example a histidine (His)-tag, a hemagglutinin (HA)-tag, or a c-Myc-tag.

Lumen: The cavity or channel within a tube, pipe, or other tubular device.

Medical device: Medical devices are objects associated with the administration of a therapy to a user. Examples of a medical device include medical infusion pumps, pulse oximeters, cardiopulmonary monitors, hemodialysis systems, and other therapy delivery and patient monitoring equipment. In some embodiments, a medical device refers to an object that is designed to be placed partially or wholly within a subject's body (an indwelling medical device, such as a device that is suitable for surgical implantation within the body) for one or more therapeutic or prophylactic purposes, such as for restoring physiological function, alleviating symptoms associated with disease, delivering therapeutic agents, detecting changes (or levels) in the internal environment, and/or repairing or replacing or augmenting damaged or diseased organs and tissues. Not all medical devices need have direct therapeutic activity. The device can be, for example, a storage device, such as a medical storage device, such as a container for a contact lens.

Pharmaceutically acceptable carriers: Conventional pharmaceutically acceptable carriers are useful for practicing the methods and forming the compositions disclosed herein. *Remington's Pharmaceutical Sciences*, by E. W. Martin, Mack Publishing Co., Easton, Pa., 15th Edition, 1975, describes examples of compositions and formulations suitable for pharmaceutical delivery of the antimicrobial compounds herein disclosed.

In general, the nature of the carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Planktonic bacteria: Single, freely suspended bacterial cells that float or swim in a liquid medium.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be found at the NCBI website.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.,* 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

Sterile: Free from living organisms and especially microorganisms such as bacteria, fungi, viruses, and protozoa.

Subject: An animal or human subjected to a treatment, observation or experiment.

Surface: The outer part or external aspect of an object, device, tissue, or organ that can interact with the environment.

Surfactant: A substance which reduces the surface tension of a liquid. In some embodiments, a surfactant added to a sample increases the solubility of organic compounds in the sample. Examples of surfactants include, but are not limited to, biosurfactants (such as glycolipids, lipopeptides, depsipeptides, phospholipids, substituted fatty acids, lipopolysaccharides, surlactin, surfactin, visconsin, and rhamnolipids), sodium dodecyl sulfate, quaternary ammonium compounds, alkyl pyridinium iodides, Tween 80, Tween, 85, Triton X-100, and the like.

Therapeutically effective amount: A quantity or concentration of a specified agent or composition sufficient to achieve a desired effect in a subject being treated. For example, this may be the amount of an antibacterial agent (for example, a *Citrobacter freundii* polypeptide, or a variant thereof) necessary to kill planktonic bacteria or surface attached bacteria (for example in a biofilm) in a subject. In another embodiment, this may be the amount of an antibacterial agent (for example, a *Citrobacter freundii* polypeptide, or a variant thereof) necessary to inhibit the growth of, or inhibit further growth, proliferation, or multiplication of planktonic bacteria or surface attached bacteria (for example in a biofilm) in a subject. In yet another embodiment, a therapeutically effective amount may be the amount of an antibacterial agent (for example, a *Citrobacter freundii* polypeptide, or a variant thereof) necessary to control growth, proliferation, or multiplication of planktonic bacteria or surface attached bacteria (for example, a biofilm) in a subject. In a further embodiment, a therapeutically effective amount may be the amount of an antibacterial agent (for example, a *Citrobacter freundii* polypeptide, or a variant thereof) necessary to reduce, or relieve the symptoms of a bacterial infection, for example caused by planktonic bacteria or surface attached bacteria (for example, a biofilm) in a subject.

In other embodiments, a therapeutically effective amount may be the amount of an antifungal agent or an antiprotozoal agent necessary to kill fungi or protozoa in a subject; inhibit the growth of; inhibit further growth, proliferation, or multiplication of fungi or protozoa in a subject; control the growth, proliferation, or multiplication of fungi or protozoa in a subject; or reduce or relieve the symptoms of a fungal infection or a protozoal infection in a subject.

Ideally, a therapeutically effective amount of a compound or composition (for example, an antimicrobial agent, an antibacterial agent, an antifungal agent, or an antiprotozoal agent) is an amount sufficient to have the effects described above without causing a substantial cytotoxic effect on non-microbial cells. However, the therapeutically effective amount of the composition or agent will be dependent on the subject being treated, the severity of the affliction, and the manner of administration of the therapeutic composition.

Treating or Treatment: A prescribed course of action (including administration of an agent, such as an antimicrobial agent or an antibacterial agent) to alter the normal course of an existing infection caused by a microorganism (for example, planktonic bacteria or surface attached bacteria, such as a biofilm). In some embodiments, the prescribed course of action is to inhibit further growth (or proliferation or multiplication) of, or control the growth (or proliferation or multiplication) of planktonic bacteria or surface attached bacteria (for example, bacteria in a biofilm). In one embodiment, treating or treatment includes a prescribed course of action on the microorganism susceptible to the treatment (for example, planktonic bacteria or surface attached bacteria). In another embodiment, treating or treatment includes a prescribed course of action to a subject infected with planktonic bacteria or a biofilm. In other embodiments, treating or treatment includes a prescribed course of action to a living surface (for example, a bone, a joint, an organ, an organ cavity, or a tissue in a subject) or a non-living surface (for example, a surface of a medical device), that contains or is in contact with the microorganism susceptible to the treatment.

As used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All sequence database references are incorporated by reference as of Jun. 21, 2011, unless specified otherwise. The materials, methods, and examples are illustrative only and not intended to be limiting.

III. Overview of Several Embodiments

Described herein is the identification of a *Citrobacter freundii* polypeptide that exhibits antibacterial activity against a wide range of Gram-negative bacteria and is effective at killing planktonic bacteria and surface attached bacteria, for example in biofilms. Thus, the disclosed *Citrobacter freundii* polypeptide, or variants thereof, can be used to inhibit the growth (or multiplication) of, inhibit further growth (or multiplication) of, or control the growth (or multiplication) of planktonic bacteria or surface attached bacteria (for example, surface attached bacteria of a biofilm).

Disclosed herein are methods for treating a biofilm by contacting the biofilm with an effective amount of an antibacterial agent. In one embodiment, the antibacterial agent is an isolated *Citrobacter freundii* colicin A polypeptide, wherein the colicin A polypeptide has an antibacterial activity against a biofilm. In another embodiment, the biofilm is on a surface of a medical device suitable for surgical implantation within a subject. In a further embodiment, a surface infected with a biofilm is selected for treatment.

Also provided herein are methods for treating a subject infected with a biofilm, by administering to the subject a therapeutically effective amount of a pharmaceutical composition comprising an antibacterial agent. In one embodiment, the antibacterial agent is a *Citrobacter freundii* colicin A polypeptide, wherein the colicin A polypeptide has an antibacterial activity against a biofilm. In another embodiment, the biofilm is on a medical device implanted in the subject. In a further embodiment, a subject infected with, or at risk of developing, a biofilm is selected for treatment. Such a subject may be, for example, a subject having an implanted medical device, such as a catheter.

In one embodiment of the disclosed methods, the colicin A polypeptide comprises an amino acid sequence at least 90% identical to the amino acid sequence set forth as SEQ ID NO: 1. In other embodiments of the methods, the medical device is a catheter, a stent, a shunt, an endotracheal tube, a gastric feeding tube, a prosthetic joint, an intrauterine device, a voice prosthesis, a central venous catheter, a tympanostomy tube, a prosthetic heart valve, or a pacemaker. In particular embodiments of the methods, treating the biofilm or the subject reduces biofilm cell viability by at least 25%, at least 50%, at least 75%, at least 80%, at least 90%, at least 95%, at least 99%, or 100%.

In some embodiments of the disclosed methods, the biofilm comprises Gram-negative bacteria. The Gram-negative bacteria include the family Enterobacteriacae. In particular embodiments, the Enterobacteriacae bacteria include a genus selected from the group consisting of *Citrobacter, Enterobacter, Escherichia, Klebsiella*, and *Yersinia*.

Some embodiments of the disclosed methods include one or more additional administrations of the *Citrobacter freundii* colicin A polypeptide, or the pharmaceutical composition comprising the *Citrobacter freundii* colicin A polypeptide, to inhibit further growth of the bacterial biofilm. Other embodiments of the disclosed methods include contacting the biofilm with an effective amount, or a therapeutically effective amount, of a second antibacterial agent, an antifungal agent, or an antiprotozoal agent.

Also provided herein is an isolated *Citrobacter freundii* colicin A polypeptide, comprising the amino acid sequence set forth as SEQ ID NO: 1, wherein the polypeptide has an antibacterial activity against a biofilm. In some embodiments, the *Citrobacter freundii* colicin A polypeptide is included in a composition or in a pharmaceutical composition. In particular embodiments, the composition or pharmaceutical composition includes one or more of a carrier, diluent, adjuvant, solubilizing agent, and suspending agent. In other embodiments, the composition or pharmaceutical composition also includes a second antibacterial agent, an antifungal agent, or an antiprotozoal agent.

Also disclosed herein is an isolated nucleic acid molecule which encodes the isolated *Citrobacter freundii* colicin A polypeptide. In one embodiment, the nucleic acid molecule has the nucleic acid sequence set forth as SEQ ID NO: 2. In another embodiment, an isolated vector comprises the nucleic acid molecule. In a further embodiment, an isolated cell comprises the vector.

Disclosed herein is a medical device where the surface of the medical device comprises an antimicrobial effective amount of the disclosed isolated *Citrobacter freundii* colicin A polypeptide. In some embodiments of the medical device, the polypeptide is incorporated into a polymeric coating on the medical device surface. In other embodiments, the polypeptide is expressed on the medical device surface by a vector comprising a nucleic acid molecule encoding the polypeptide.

IV. Methods of Treating Infections Caused by Planktonic Bacteria or Biofilms Multi- and pan-antibiotic resistant bacteria are a major health challenge in hospital settings. Furthermore, when planktonic bacteria that are susceptible or sensitive to antibacterial agents establish surface attached biofilm populations, they become less sensitive or resistant to antimicrobial therapy. Bacterial biofilm formation can lead to localized infections as well as difficult to treat, and sometimes fatal, systemic infections, such as bacteremia (the presence of bacteria in the blood) and bacterial sepsis (multiple organ failure caused by the spread of bacteria or their products through the bloodstream). The extracellular substances that comprise the biofilm matrix can act as a barrier that protects and isolates the bacteria resident within the biofilm from normal immunological defense mechanisms, such as antibodies and phagocytes, as well as from antimicrobial agents including surfactants, antibacterial enzymes and antibiotics. The biofilm also facilitates the growth and proliferation of bacteria resident within the biofilm. Therefore there is an urgent need for novel antimicrobials (for example, antibacterials) that are effective against multi-drug resistant planktonic bacteria and/or biofilms containing surface attached bacteria.

It has been surprisingly demonstrated that the disclosed *Citrobacter freundii* polypeptide exhibits antibacterial activity against a wide range of Gram-negative bacteria and is effective at killing planktonic bacteria and bacteria in biofilms. Thus, the disclosed *Citrobacter freundii* polypeptide, or variants thereof, can be used to inhibit the growth (or multiplication) of, inhibit further growth (or multiplication) of, or control the growth (or multiplication) of planktonic bacteria or surface attached bacteria (for example, surface attached bacteria within a biofilm).

Disclosed herein is a method for treating an infection caused by a biofilm or planktonic bacteria. In a one embodiment of the method, a surface infected with a biofilm is selected for treatment. In a particular embodiment, the method involves contacting a biofilm with an effective amount of the disclosed *Citrobacter freundii* polypeptide, or variants thereof, wherein the *Citrobacter freundii* polypeptide or variants thereof, has an anti-bacterial activity against the biofilm, thereby treating the biofilm. In another embodiment of the method, contacting a biofilm involves contacting a mass, aggregation, or community of microorganisms attached to a surface and the associated extracellular substances produced by one or more of the attached bacteria. In one embodiment, the biofilm is a bacterial biofilm. In a specific, non-limiting example, the bacterial biofilm is recalcitrant (or resistant) to antimicrobial or antibacterial treatments that are normally effective at inhibiting or controlling the growth of its planktonic counterpart. Alternatively, at the first indication of biofilm formation, the methods may be used to inhibit further biofilm formation (or growth or multiplication).

In particular embodiments of the method, a bacterial biofilm causing the infection to be treated is an integrated community of a plurality (two or more) of species of bacteria (for example, a polymicrobic biofilm). In other embodiments, a bacterial biofilm is a community that includes a single species of bacteria or a community that is populated predominantly by a single species of bacteria.

In some embodiments of the method, the extracellular substances of the biofilm are polymeric substances that include a matrix of complex polysaccharides, bacterial genomic DNA, proteinaceous substances, and glycopeptides. In some embodiments, extracellular polysaccharides differ, for example, by the type of sugar monomers, the kind of linkage between monomers, and subunits incorporated into the polysaccharide. Particular examples of extracellular polysaccharides include, but are not limited to, alginate, PEL, and PSL (all three produced by *Pseudomonas aeruginosa*), as well as poly-N-acetyl glucosamine (PNAG)/polysaccharide intercellular adhesion (PIA) and vibrio polysaccharide (VPS). Particular examples of extracellular proteins include, but are not limited to, curli protein, fibronectin binding protein A, fimbriae protein, flagellar protein, large adhesion protein A (LapA), and type IV pilus protein.

In another embodiment, the method involves contacting planktonic bacteria, for example a planktonic culture, with an effective amount of the disclosed *Citrobacter freundii* A polypeptide, or variants thereof, wherein the *Citrobacter freundii* polypeptide or variants thereof, has an anti-bacterial activity against the planktonic bacteria, thereby treating the planktonic bacteria.

In particular embodiments of the method, an infection caused by a biofilm to be treated may include other microorganisms. Such microorganisms include, but are not limited to, fungi and/or protozoa. The nature of a biofilm, such as its structure and composition, may depend on the particular species of microorganism (for example, bacteria, fungi, and/or protozoa) present in the biofilm.

In one embodiment of the method, bacteria present in a biofilm to be treated may be genetically or phenotypically different than their planktonic counterpart. In one embodiment, the bacteria in the biofilm are Gram-negative bacteria. Examples of Gram-negative bacteria include *Escherichia, Salmonella, Shigella, Pseudomonas, Moraxella, Helicobacter, Stenotrophomonas, Bdellovibrio, Legionella* and *Wolbachia*. Specific, non-limiting examples of Gram-negative bacterial species include *Citrobacter freundii, Pseudomonas aeruginosa, Legionella pneumophila, Escherichia coli, Klebsiella pneumoniae, Proteus mirabilis, Hemophilus influenzae, Enterobacter cloacae, Serratia marcescens, Helicobacter pylori, Acinetobacter baumannii, Neisseria gonorrhoeae, Neisseria meningitidis, Moraxella catarrhalis, Salmonella enteritidis*, and *Salmonella typhi*. In a particular embodiment, the bacteria are of the family Enterobacteriacae. Specific, non-limiting examples of Enterobacteriacae include the genus *Citrobacter, Enterobacter, Escherichia, Klebsiella, Salmonella, Shigella*, and *Yersinia*. In another embodiment, the bacteria in the biofilm are Gram-positive bacteria. Specific, non-limiting examples of Gram-positive bacteria include *Staphylococcus, Streptococcus, Enterococcus, Bacillus, Corynebacterium, Nocardia, Clostridium*, and Actinobacteria. In one embodiment, the Gram-positive bacteria in the biofilm does not include *Listeria*.

In one embodiment of the method, contacting a biofilm or planktonic bacteria with a disclosed *Citrobacter freundii* polypeptide, or variants thereof, involves administering to the biofilm or planktonic bacteria a *Citrobacter freundii* colicin A polypeptide. In another embodiment, contacting a biofilm or planktonic bacteria with a disclosed *Citrobacter freundii* polypeptide, or variants thereof, involves administering to the biofilm or planktonic bacteria a *Citrobacter freundii* CfbX polypeptide (SEQ ID NO: 1). In another embodiment of the method, the *Citrobacter freundii* polypeptide administered to the biofilm or planktonic bacteria is at least 70% identical to the amino acid sequence set forth as SEQ ID NO: 1. In other embodiments of the method, the polypeptide is at least 75%, at least 80%, at least 85%, at least 90%, at least 95%, at least 96%, at least 97%, at least 98%, or at least 99% identical to the amino acid sequence set forth as SEQ ID NO: 1. In a further embodiment of the method, the *Citrobacter freundii* polypeptide administered to the biofilm or planktonic bacteria is encoded by the cfbx nucleic acid sequence (SEQ ID NO: 2). In other embodiments, the nucleic acid sequence is at least 70%, at least 80%, at least 85%, at least 90%, at least 95%, at least 96%, at least 97%, at least 98%, or at least 99% identical to the nucleic acid sequence set forth as SEQ ID NO: 2. In particular embodiments of the method, the *Citrobacter freundii* polypeptide, or a variant thereof, does not have the same amino acid sequence as the *E. coli* K-12 colicin E2 polypeptide.

In some embodiments, the disclosed *Citrobacter freundii* polypeptide, or variants thereof, used in the methods is purified, for example from the *Citrobacter freundii* bacteria that produces, expresses or secretes it, or from a host cell that produces, expresses, or secretes a recombinant form of the *Citrobacter freundii* polypeptide. In other embodiments, the disclosed *Citrobacter freundii* polypeptide, or variants thereof, is in a cell extract from the *Citrobacter freundii* bacteria that produces, expresses, or secretes it or from a host cell (for example, a non-pathogenic strain of *E. coli* or another member of the Enterbacteriaciae family) that produces, expresses, or secretes a recombinant form of the polypeptide. In yet other embodiments, the disclosed *Citrobacter freundii* polypeptide, or variants thereof, is in an extract from the media into which the *Citrobacter freundii* bacteria secretes the polypeptide (either the natural or the recombinant form of the polypeptide).

It is envisioned that in some embodiments of the method, a *Citrobacter freundii* colicin polypeptide other than the disclosed CfbX polypeptide can be used to treat an infection caused by a biofilm or planktonic bacteria. It is also envisioned that a colicin polypeptide from a microorganism other than *Citrobacter freundii* can be used to treat an infection caused by a biofilm or planktonic bacteria. In some embodiments of the method, the colicin polypeptide is a Group A colicin (for example, colicin A, E1, E2, E3, E4, E5, E6, E7, E8, E9, K, N, U, or Cloacin DF13) from any colicin-producing microorganism. In other embodiments, the colicin polypeptide is a Group B colicin (for example, colicin B, D, Ia, Ib, M, 5-10) from any colicin-producing microorganism.

As disclosed herein, the *Citrobacter freundii* polypeptide, or a variant thereof, has an anti-bacterial activity against a biofilm or planktonic bacteria. In one embodiment, an antimicrobial activity is an increase in cell lysis. Thus, in one embodiment of the method, contacting the biofilm or planktonic cells with the disclosed *Citrobacter freundii* polypeptide, or a variant thereof, increases bacterial cell lysis in the biofilm, or increases lysis of planktonic bacterial cells, compared to a biofilm or planktonic cells not contacted with the *Citrobacter freundii* polypeptide. In particular embodiments, an increase in bacterial cell lysis is at least a 2%, at least a 5%, at least a 10%, at least a 20%, at least a 30%, at least a 40%, at least a 50%, at least a 75%, at least a 100%, at least a 150%, at least a 200% or more increase in lysed cells in the biofilm. In further embodiments, an increase in bacterial cell lysis is at least 2%, at least 5%, at least 10%, at least 20%, at least a 30%, at least a 40%, at least a 50%, at least a 75%, at least a 100%, at least a 150%, at least a 200% or more increase in lysed planktonic bacterial cells. In another embodiment, an antibacterial activity is a reduction in biofilm cell viability or planktonic bacteria cell viability, compared to biofilm cells or planktonic bacteria cells not contacted with the *Citrobacter freundii* polypeptide. In particular embodiments, a reduction in cell viability is a reduction of viable cells by at least a 2%, at least a 5%, at least a 10%, at least a 20%, at least 25%, at least 50%, at least 75%, at least 80%, at least 90%, at least 95%, at least 96%, at least 97%, at least 98%, at least 99%, or 100%. In further particular embodiments, a reduction in biofilm cell viability or planktonic bacteria cell viability (or an increase in bacterial cell lysis) is a reduction in bacterial cell number in the biofilm or a reduction in planktonic bacteria cell number by at least a 2%, at least a 5%, at least a 10%, at least a 20%, at least 25%, at least 50%, at least 75%, at least 80%, at least 90%, at least 95%, at least 96%, at least 97%, at least 98%, at least 99%, or 100%. In one specific non-limiting example, the antibacterial activity of the *Citrobacter freundii* polypeptide, or a variant thereof, can be measured by the production or the size (for example, the diameter) of a clear zone on a microbial lawn surrounding a bacterial colony that produces, expresses, or secretes the *Citrobacter freundii* polypeptide, or a variant thereof.

In some embodiments of the method, the biofilm is attached to a living or non-living surface. In some embodiments, the living or non-living surface is in a subject. In particular embodiments, a living surface in the subject is a surface of an organ or tissue in the subject. In specific non-limiting examples, the living surface is a surface in the middle ear, in a chamber of the heart, on a heart valve, in the lungs, on the skin (for example, in a skin wound), in a nasal sinus, or in the mouth (for example, on one or more teeth). In other particular embodiments, a non-living surface in the subject is a surface of a medical device, such as the surface of an indwelling medical device. Examples of indwelling medical devices include intravascular catheters (for example, intravenous and intra-arterial), right heart flow-directed catheters, Hickman catheters, arteriovenous fistulae, catheters used in hemodialysis and peritoneal dialysis (for example, silastic, central venous, Tenckhoff, and Teflon catheters), vascular access ports, indwelling urinary catheters, urinary catheters, silicone catheters, ventricular catheters, synthetic vascular prostheses (for example, aortofemoral and femoropopliteal), prosthetic heart valves, prosthetic joints (for example, prosthetic knee or hip joints), orthopedic implants, penile implants, shunts (for example, Scribner, Torkildsen, central nervous system, portasystemic, ventricular, ventriculoperitoneal), intrauterine devices, dental prostheses (for example, permanent dentures or partial implants), stents (for example, ureteral stents), artificial voice prostheses, tympanostomy tubes, gastric feeding tubes, endotracheal tubes, pacemakers, implantable defibrillators, tubing, cannulas, probes, blood monitoring devices, needles, mouth guards, night guards, dentures, orthodontic retainers, contact lenses, and the like.

The indwelling medical device can be completely embedded in the subject (for example, a prosthetic joint, a prosthetic heart valve, or a pacemaker). In some embodiments, the indwelling medical device has both internal and external parts, relative to the subject (for example, a urinary catheter, a gastric feeding tube, or a dental implant). In particular embodiments, the indwelling medical devices include surgically implantable devices (for example, a pacemaker, prosthetic heart valves, shunts, prosthetic joints, orthopedic implants, dental implants or synthetic vascular prostheses). In other particular embodiments, the indwelling medical device is not surgically implanted, but is routinely inserted and removed by the subject (for example, a mouth guard, a night guard, removable dentures, an orthodontic retainer, or a contact lens). In further embodiments, the indwelling medical device can be removed from the body, for example to treat a biofilm infection on a surface of the device. In some embodiments, the medical device has a lumen (for example, a catheter).

However, the medical device need not be implantable, nor need it have direct therapeutic activity. The device can be, for example, a storage device, such as a medical storage device, for example a container for a contact lens.

In other embodiments of the method, the non-living surface to be treated is a surface of an object that is not a medical device. In particular embodiments, the non-living surface is on or near a food preparation area (for example, a counter, a table, or a floor), on food preparation utensils (for example, a knife), on a household surface (for example, a shower or a toilet), or a fluid-conducting or gas-conducting object having a lumen (such as a water, oil, gas, or sewage pipe or tubing).

In one embodiment of the method, the medical device to be treated is suitable for surgical implantation within the body of the subject. In another embodiment of the method, the medical device is surgically implanted within the body of the subject. In a further embodiment, the medical device is non-permanently inserted in the subject. In yet a further embodiment, the medical device is not introduced, inserted, or surgically implanted in the subject.

The living or non-living surfaces can have surfaces composed of thermoplastic or polymeric materials such as polyethylene, Dacron, nylon, polyesters, polytetrafluoroethylene, polyurethane, latex, silicone elastomers, and the like. The surfaces may be smooth or rough, for example, a smooth polymeric surface of a catheter lumen or a relatively rough Dacron patch for repairing an abdominal or vascular defect. Metallic surfaces are also amenable to treatment with the disclosed compositions.

Various methods can be employed to treat an infection on the living or non-living surfaces with the disclosed *Citrobacter freundii* polypeptide, or a variant thereof. In some embodiments of the method, the disclosed *Citrobacter freundii* polypeptide, or a variant thereof, is administered to the non-living surface before a biofilm is formed in order to inhibit the formation of a biofilm on the surface. The disclosed *Citrobacter freundii* polypeptide, or a variant thereof, may be applied to (for example, a composition comprising the *Citrobacter freundii* polypeptide, or a variant thereof, may be painted, sprayed, or soaked on) the living or non-living surface. In particular embodiments, the living or non-living surface is dipped or immersed in a composition (for example, a polymeric coating) comprising the *Citrobacter freundii* polypeptide, or a variant thereof. In other embodiments, the composition comprising the *Citrobacter freundii* polypeptide, or a variant thereof, is applied to the living or non-living surface with an adhesive, for example a biological adhesive, such as fibrin glue. In a further embodiment, the composition is applied to the surface in a powder. One specific, non-limiting example of the method is to flush the lumen of a medical device with a composition containing the disclosed *Citrobacter freundii* polypeptide, or a variant thereof. In particular embodiments of the method, the flushing solution is composed of sterile media or sterile normal saline solutions in addition to the disclosed *Citrobacter freundii* polypeptide, or a variant thereof.

The polymers of the compositions (i.e. polymeric coatings) may be biodegradable or non-biodegradable. Non-limiting examples of suitable non-biodegradable polymers include polystyrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such coatings may be formed by any method known to one in the art. For example, an initial polymer/solvent mixture can be formed and then the disclosed *Citrobacter freundii* polypeptide, or a variant thereof, added to the polymer/solvent mixture. Alternatively, the polymer, solvent, and *Citrobacter freundii* polypeptide, or a variant thereof, can be added simultaneously to form the mixture.

The polymer/solvent/polypeptide mixture may be a dispersion, suspension or a solution. The polypeptide may also be mixed with the polymer in the absence of a solvent. The polypeptide may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents, such as an antibiotic, a bacteriocin, an antimicrobial peptide, a predatory bacteria, or a bacteriophage.

In some embodiments, the coating is from about 1 to about 50 microns thick. In other embodiment, the coating is very thin, such as about 0.2-0.3 microns. In yet other embodiments, the coating is more than 10 microns. Multiple layers of polymer coatings can be applied onto the medical device. Such multiple layers may contain the same or different therapeutic agents and/or the same or different polymers. Methods of choosing the type, thickness and other properties of the polymer and/or therapeutic agent to create different release kinetics are well known to one in the art.

A living or non-living surface may require the controlled release of the *Citrobacter freundii* polypeptide, or a variant thereof. Thus, in some embodiments of the method, the composition includes a time-release formulation, such that the polypeptide is released over an extended period of time (for example, weeks, months, or years). In further embodiments of the method, the ability to control release of the *Citrobacter freundii* polypeptide, or a variant thereof, is by manipulation of one or more features of the controlled release device, including formulation of the coating composition, duration of time the device is maintained at the implantation site, and configuration of the device. For example, the controlled delivery device can be maintained at an implantation site for any desired amount of time, and the release kinetics of the *Citrobacter freundii* polypeptide, or a variant thereof, can be adjusted to deliver the total amount of polypeptide, at the desired rate, to achieve a desired effect (for example, preventing biofilm formation, treating a device infected with a biofilm, treating a subject infected with a biofilm).

In other embodiments, a recombinant vector containing a polynucleotide encoding a *Citrobacter freundii* polypeptide, or a variant thereof, for use in accordance with embodiments disclosed herein, is applied to the living or non-living surface. In one specific, non-limiting example, the polynucleotide may be introduced into a cell-free expression system known in the art for producing peptides or polypeptides. In another example, applied to the living or non-living surface is a vector into which is introduced a desired nucleic acid sequence encoding a *Citrobacter freundii* polypeptide, or a variant thereof, such that upon expression, the gene product prevents or inhibits the growth of a biofilm. In some embodiments, the polypeptide is expressed over an extended period of time (for example, weeks, months, or years).

In some embodiments of the method, the medical device is removed from the subject prior to treatment of the subject and/or the medical device. In other embodiments of the method, the subject is administered the disclosed *Citrobacter freundii* polypeptide, or a variant thereof. Without being bound by theory, the disclosed methods improve the operability or reduce the infectious potential of a medical device, or reduce the occlusion of a pipe or tubing, caused by the growth or encrustation of the biofilm on the surface.

The methods disclosed herein can be used to treat subjects having, or at risk of, developing a bacterial infection (for example, patients infected by planktonic bacteria or infected with a biofilm). In one embodiment, a subject infected with planktonic bacteria or a biofilm is selected for treatment. In some embodiments, the subject is identified because of clinical symptoms associated with a bacterial infection (for example, but not limited to, fever, malaise, pain, redness, nausea, vomiting, diarrhea, swelling, cough, or elevated white blood cell count) or because an indwelling device is not operating properly (for example, but not limited to, occlusion of a catheter). In particular embodiments of the method, the subject is administered the disclosed *Citrobacter freundii* polypeptide, or a variant thereof, to treat the planktonic bacteria or the biofilm in the subject. In specific, non-limiting examples, the administration of the disclosed *Citrobacter freundii* polypeptide, or a variant thereof, treats bacterial sepsis or bacteremia in the subject.

In some embodiments, the methods disclosed herein can be used to treat subjects having inserted or implanted or indwelling medical devices (including long term use, or permanently or semi-permanently implanted devices) to inhibit, control the growth of, or eliminate a biofilm on a surface of the medical device. Thus, also disclosed herein is a method of treating a subject by administering to the subject the disclosed *Citrobacter freundii* polypeptide, or a variant thereof.

In some embodiments of disclosed methods, the medical device is intended to be inserted or implanted in the subject for at least 1 week, at least 2 weeks, at least 3 weeks, at least 4 weeks, at least 1 month, at least 2 months, at least 3 months, at least 4 months, at least 5 months, at least 6 months, at least 1 year, at least 2 years, at least 3 years, at least 5 years, at least 10 years, at least 20 years, at least 30 years, or more. In other embodiments of the present disclosure, the medical device is intended to be inserted or implanted in the subject from about 7 days to about 30 years, from about 7 days to about 10 years, from about 7 days to about 5 years, from about 7 days to about 2 years, from about 7 days to about 1 year, or from about 7 days to about 6 months. In further embodiments of the present disclosure, the medical device is intended to be inserted or implanted in the subject from about 6 months to about 30 years, from about 6 months to about 10 years, from about 6 months to about 5 years, from about 6 months to about 2 years, or from about 6 months to about 1 year. In yet further embodiments of the present disclosure, the medical device is intended to be inserted or implanted in the subject from about 1 year to about 30 years, from about 1 year to about 10 years, from about 1 year to about 5 years, from about 1 year to about 4 years, from about 1 year to about 3 years, or from about 1 year to about 2 years. In other embodiments of disclosed method, the medical device is intended to be inserted or implanted in the subject for no more than 1 week, no more than 2 weeks, no more than 3 weeks, no more than 4 weeks, no more than 1 month, no more than 2 months, no more than 3 months, no more than 4 months, no more than 5 months, no more than 6 months, no more than 1 year, no more than 2 years, no more than 3 years, no more than 5 years, no more than 10 years, no more than 20 years, no more than 30 years, or no more than 40 years.

In some embodiments of the methods, the disclosed *Citrobacter freundii* polypeptide, or a variant thereof, can be administered one or more times to a non-living surface, a living surface, or a subject infected with a planktonic bacteria or a biofilm. For example, the disclosed *Citrobacter freundii* polypeptide, or a variant thereof, can be administered at least once, at least twice, at least three times, at least four times, at least five times, at least ten times, at least fifteen times, at least twenty times or more.

In other embodiments, the disclosed *Citrobacter freundii* polypeptide, or a variant thereof, can be co-administered, simultaneously or alternately, with one or more additional agents. The additional agent can be an antimicrobial agent, such as antibacterial agents (for example, an antibiotic, a bacteriocin, an antimicrobial peptide, a predatory bacteria, or a bacteriophage), anti-fungal agents, anti-protozoal agents, or combinations thereof. Exemplary antibiotics include, but are not limited to, an aminoglycoside, an ansamycin, a beta-lactam, a carbacephem, a carbapenem, a cephalosporin, a lincosamide, a macrolide, a monobactam, a nitrofuran, a penicillin, a quinolone, a sulfonamide, a tetracycline, a silver salt, and the like. Examples of bacteriocins include, but are not limited to, agrocin, alveicin, aureocin, carnocin, colicin, curvaticin, divercin, enterocin, enterolysin, epidermin, erwiniocin, glycinecin, halocin, lactococin, lacticin, leucoccin, mesentericin, nisin, pediocin, plantaricin, sakacin, subtilin, sulfolobicin, thuricin 17, trifolitoxin, vibriocin, and warnerin. Examples of bacteriophages include, but are not limited to, λ phage, T1 phage, T2 phage, T3 phage, T4 phage, T5 phage, T6 phage, and T7 phage. Examples of anti-fungal agents include, but are not limited to, miconozole, ketoconazole, clotrimazole, exonazole, omoconazole, oxiconazole, sertconazole, sulconazole, fluconazole, itraconazole, ravuconazole, teraconazole, abafungin, terbinafine, naftifine, butenafine, aniudulafungin, micafungin, benzoic acid, polygodial, tolnaftate, and ciclopirox. Examples of antiprotozoal agents include, but are not limited to, Metronidazole, Eflornithine, Furazolidone, Hydroxychloroquine, Iodoquinol, Yodoquinol, Pentamidine, Melarsoprol, Metronidazole, Ornidazole, Paromomycin sulfate, Pyrimethamine, anf Tinidazole.

In further embodiments, the additional agent used is to facilitate removing the biofilm deposited on a surface. For example, the compositions can include a surfactant or an antibacterial enzyme, or combinations thereof. Exemplary surfactants include, but are not limited to, biosurfactants (such as glycolipids, lipopeptides, depsipeptides, phospholipids, substituted fatty acids, lipopolysaccharides, surlactin, surfactin, visconsin, and rhamnolipids), sodium dodecyl sulfate, quaternary ammonium compounds, alkyl pyridinium iodides, Tween 80, Tween, 85, Triton X-100, hexadecyl pyridinium chloride, polysorbates, sorbitans, poly(oxyethylene) alkyl ethers, poly(oxyethylene)alkyl esters, and the like. Exemplary antibacterial enzymes are, but not limited to, a lytic enzyme, an acylase, an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, and lysostaphin.

V. Compositions for Treating Infections Caused by Planktonic Bacteria or Biofilms Disclosed herein is an antibacterial agent isolated from *Citrobacter freundii*. The disclosed *Citrobacter freundii* antibacterial agent exhibits bacteriocidal and/or bacteriostatic activity against a wide range of Gram-negative bacteria and is surprisingly effective at killing or suppressing the growth of planktonic bacteria or bacteria in biofilms. Thus, the disclosed agent can be used to kill, inhibit the growth (or multiplication) of, inhibit further growth (or multiplication) of, or control the growth (or multiplication) of planktonic bacteria or surface attached bacteria (for example, surface attached bacteria of a biofilm).

In some embodiments, the *Citrobacter freundii* antibacterial agent disclosed herein is a polypeptide that exhibits antibacterial activity. In particular embodiments, the *Citrobacter freundii* polypeptide is a *Citrobacter freundii* colicin A polypeptide. In one specific embodiment, the *Citrobacter freundii* colicin A polypeptide is a CfbX polypeptide (SEQ ID NO: 1). Without being bound by theory, the amino (NH$_2$)-terminal region of CfbX (residues 1 to 172) is involved in translocating the *Citrobacter freundii* antibacterial agent through the outer membrane of a susceptible bacterial cell; the central region of CfbX (residues 173 to 336) contains the cell-surface receptor-binding domain, and the carboxy (COOH)-terminal domain (residues 389 to 592) carries the pore-forming activity of the *Citrobacter freundii* antibacterial agent.

Variants of the disclosed *Citrobacter freundii* polypeptide are envisioned herein. In one embodiment, the *Citrobacter freundii* polypeptide is at least 70% identical to the amino acid sequence set forth as SEQ ID NO: 1. In other embodiments, the polypeptide is at least 75%, at least 80%, at least 85%, at least 90%, at least 95%, at least 96%, at least 97%, at least 98%, or at least 99% identical to the amino acid sequence set forth as SEQ ID NO: 1. Variants of the disclosed *Citrobacter freundii* polypeptide demonstrate the antibacterial activity of the *Citrobacter freundii* CfbX polypeptide. In particular embodiments of the disclosed *Citrobacter freundii* polypeptide, the *Citrobacter freundii* polypeptide, or a variant thereof, does not have the same amino acid sequence as the *E. coli* K-12 colicin E2 polypeptide.

In some examples, the *Citrobacter freundii* polypeptide is about 4 to 8, such as 5 to 7, amino acids in length to about 592 amino acids in length, such as between about 10 to about 592, about 10 to 5 about 50, about 10 to about 500, about 10 to about 400, about 10 to about 300, about 10 to about 200, about 10 to about 100, about 10 to about 50, about 50 to about 550, about 50 to about 500, about 50 to about 400, about 50 to about 300, about 50 to about 200, about 50 to about 100, about 100 to about 550, about 100 to about 500, about 100 to about 400, about 100 to about 300, about 100 to about 200, about 200 to about 550, about 200 to about 500, about 200 to about 400, about 200 to about 300, about 300 to about 550, about 300 to about 500, about 300 to about 400, about 400 to about 550, about 400 to about 500 amino acids in length. In some examples, the *Citrobacter freundii* polypeptide is no more than about 5, about 10, about 15, about 20, about 30, about 40, about 50, about 60, about 70, about 80, about 90, about 100, about 110, about 120, about 130, about 140, about 150, about 200, about 250, about 300, about 350, about 400, about 450, about 500, about 550, about 560, about 570, about 580, about 590, or about 592 amino acids in length.

In some examples, the *Citrobacter freundii* polypeptide is about 4 to 8, such as 5 to 7, amino acids in length to about 592 amino acids in length of SEQ ID NO: 1. In other examples, the *Citrobacter freundii* polypeptide is about 163 amino acids in length, about 172 amino acids in length, or about 203 amino acids in length. In particular examples, the *Citrobacter freundii* polypeptide corresponds to residues 1-172 of SEQ ID NO: 1, residues 173-336 of SEQ ID NO: 1, or residues 389-592 of SEQ ID NO: 1, or variants thereof. In one embodiment, the *Citrobacter freundii* polypeptide does not have a substitution at residue 327 of SEQ ID NO: 1. In another embodiment, the *Citrobacter freundii* polypeptide does not have a leucine at position 327 of SEQ ID NO: 1. In yet a further embodiment, *Citrobacter freundii* polypeptide has a serine at position 327 of SEQ ID NO: 1.

In a further embodiment, the *Citrobacter freundii* polypeptide is encoded by the cfbx nucleic acid sequence (SEQ ID NO: 2). In other embodiments, the nucleic acid sequence is at least 90%, at least 95%, at least 96%, at least 97%, at least 98%, or at least 99% identical to the nucleic acid sequence set forth as SEQ ID NO: 2. Manipulation of the cfbx nucleic acid sequence using standard procedures (including, but not limited to site-directed mutagenesis or PCR), can be used to produce such variants. The simplest modifications involve the substitution of one or more nucleotides that results in the substitution of one or more amino acids for amino acids having similar biochemical properties (conservative substitutions). Variants of the disclosed *Citrobacter freundii* cfbx nucleic acid sequence encode a polypeptide that demonstrates the antibacterial activity of the *Citrobacter freundii* CfbX polypeptide.

In some examples, the nucleic acid sequence encoding the *Citrobacter freundii* polypeptide is about 12 to 24, such as 15 to 21, nucleic acid residues in length to about 1779 nucleic acids in length of SEQ ID NO: 2. In other examples, nucleic acid sequence encoding the *Citrobacter freundii* polypeptide is about 250 nucleic acids in length, about 500 nucleic acids in length, about 1000 nucleic acids in length, about 1500 nucleic acids in length, or about 1750 nucleic acids in length. In particular examples, the nucleic acid sequence encoding *Citrobacter freundii* polypeptide corresponds to residues 1-516 of SEQ ID NO: 2, residues 517-1008 of SEQ ID NO: 2, or residues 1167-1776 of SEQ ID NO: 2. In one embodiment, the nucleic acid sequence encoding *Citrobacter freundii* polypeptide does not have a substitution at residue 980 of SEQ ID NO: 2. In another embodiment, the nucleic acid sequence encoding *Citrobacter freundii* polypeptide does not have a thymine at residue 980 of SEQ ID NO: 2. In a further embodiment, the nucleic acid sequence encoding *Citrobacter freundii* polypeptide does not have a codon that encodes a leucine at residues 979-981 of SEQ ID NO: 2.

The disclosed *Citrobacter freundii* polypeptide can be coupled to a targeting moiety to provide a chimeric molecule that preferentially directs the *Citrobacter freundii* polypeptide to a target cell (e.g., a bacterial colony, a bacterium, a population of target microorganisms, a biofilm, and the like), for example a target planktonic bacteria or target biofilm. In addition, the disclosed *Citrobacter freundii* polypeptide can be coupled to a detecting moiety to provide a chimeric molecule that can be used to detect or isolate the *Citrobacter freundii* polypeptide. Thus, the present disclosure encompasses *Citrobacter freundii* polypeptide fusion proteins. A fusion protein is a protein comprising two or more amino acid sequences that are not found joined together in nature (i.e. two or more heterologous amino acid sequences). *Citrobacter freundii* polypeptide fusion proteins specifically comprise at least (i) the amino acid sequence shown in SEQ ID NO: 1 or a sequence sharing at least 90%, at least 95%, at least 98%, or at least 99% sequence identity with SEQ ID NO: 1, and (ii) a peptide portion placed at either end of or within the amino acid sequence shown in SEQ ID NO: 1 or a sequence sharing at least 90%, at least 95%, at least 98%, or at least 99% sequence identity with SEQ ID NO: 1. Such *Citrobacter freundii* polypeptide fusion proteins can additionally include other protein elements, such as a linker between the heterologous peptide portions.

Fusion proteins are of use, for example, when a protein of interest is present in very small quantities, and protein quantities are insufficient for characterizing the protein, raising antibodies against the protein, purifying the protein, or utilizing the protein for therapeutic purposes. By fusing the nucleic acid sequence encoding a known protein or peptide with the nucleic acid sequence of the *Citrobacter freundii* polypeptide of interest, fusion proteins can be produced in culture in large quantities.

In some embodiments, a DNA sequence which codes for the *Citrobacter freundii* polypeptide of interest is tagged or fused with the sequence for another protein (for example, green fluorescent protein; GFP) or a sequence that codes for an identifiable peptide tag (for example, HA (hemagglutinin), histidine-tag, or c-Myc). To isolate or to localize the protein of interest, the tag, which is now part of the protein, is isolated or localized. In certain embodiments, agarose bound anti-HA or anti-c-Myc is used to isolate the fusion protein from a culture supernatant or cell lysate. Biotinylated antibodies are used to identify the proteins of interest in western blots or potentially to localize the fusion proteins in the tissue. These and other methods of creating and detecting fusion proteins are known to those of skill in the art.

In some embodiments, the disclosed *Citrobacter freundii* polypeptide, or variants thereof, are purified, for example from the *Citrobacter freundii* bacteria that produces, secretes, or expresses it or from a host cell that produces, secretes, or expresses a recombinant form of the *Citrobacter freundii* polypeptide. In other embodiments, the disclosed *Citrobacter freundii* polypeptide, or variants thereof, are in a cell extract from the *Citrobacter freundii* bacteria that produces, secretes, or expresses it or from a host cell that expresses, produces, or secretes a recombinant form of the polypeptide.

In some embodiments, a composition including the disclosed *Citrobacter freundii* polypeptide, or variants thereof, also includes an additional agent. The additional agent can be an antimicrobial agent, such as an antibacterial agent (for example, an antibiotic, a bacteriocin, an antimicrobial peptide, or a bacteriophage), an anti-fungal agent, and anti-protozoal agent, or combinations thereof (as described in the section above). The disclosed antimicrobial agents can be contained and/or provided in any media, buffer, or solution known to one of skill in the art.

VI. Pharmaceutical Compositions

Pharmaceutical compositions that include the disclosed antimicrobial agents (for example antibacterial agents, antifungal agents, or antiprotozoal agents, or combinations thereof) can be formulated with an appropriate pharmaceutically acceptable carrier, depending upon the particular mode of administration chosen. In one embodiment, an antibacterial agent, for example the disclosed *Citrobacter freundii* polypeptide, or variants thereof, can be formulated with an appropriate pharmaceutically acceptable carrier, depending upon the particular mode of administration chosen. In other embodiments, an antibacterial agent, for example the disclosed *Citrobacter freundii* polypeptide, or variants thereof, in combination with an additional antimicrobial agent (for example, at least one, at least two, at least three, or more additional antimicrobial agents) can be formulated with an appropriate pharmaceutically acceptable carrier, depending upon the particular mode of administration chosen. In one example, the pharmaceutical composition includes the *Citrobacter freundii* polypeptide, or a variant thereof, and a pharmaceutically acceptable carrier. In other examples, the pharmaceutical composition includes the *Citrobacter freundii* polypeptide, or a variant thereof, an additional antimicrobial agent, and a pharmaceutically acceptable carrier. In some examples, the pharmaceutical composition consists essentially of the *Citrobacter freundii* polypeptide, or a variant thereof, and a pharmaceutically acceptable carrier. In the present disclosure, "consists essentially of" indicates that additional active compounds (for example additional antimicrobial agents) are not included in the composition, but that other inert agents (such as fillers, wetting agents, or the like) can be included, and "consists of" indicates that additional agents are not included in the composition.

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually comprise injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

In some embodiments, the *Citrobacter freundii* polypeptide or a variant thereof is included in a controlled release formulation, for example, a microencapsulated formulation. Various types of biodegradable and biocompatible polymers, methods can be used, and methods of encapsulating a variety of synthetic compounds, proteins and nucleic acids, have been well described in the art (see, for example, U.S. Pat. Publication Nos. 2007/0148074; 2007/0092575; and 2006/0246139; U.S. Pat. Nos. 4,522,811; 5,753,234; and 7,081,489; PCT Publication No. WO/2006/052285; Benita, *Microencapsulation: Methods and Industrial Applications*, $2^{nd}$ ed., CRC Press, 2006).

In other examples, the *Citrobacter freundii* polypeptide or a variant thereof is included in a nanodispersion system. Nanodispersion systems and methods for producing such nanodispersions are well known to one of skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid) (PLGA), poly(ethylene glycol). Exemplary low molecular weight surfactants include sodium dodecyl sulfate, hexadecyl pyridinium chloride, polysorbates, sorbitans, poly(oxyethylene)alkyl ethers, poly(oxyethylene)alkyl esters, and combinations thereof. In some examples, the nanodispersion is prepared using the solvent evaporation method. See, e.g., Kanaze et al., *Drug Dev. Indus. Pharm.* 36:292-301, 2010; Kanaze et al., *J. Appl. Polymer Sci.* 102:460-471, 2006.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The pharmaceutical compositions that include an antimicrobial agent, for example a *Citrobacter freundii* polypeptide or a variant thereof, can be formulated in unit dosage form, suitable for individual administration of precise dosages. In specific, non-limiting examples, a unit dosage contains from about 1 microgram to about 1 g of an antimicrobial agent (for example, a *Citrobacter freundii* polypeptide), such as about 50 micrograms to about 900 mg, about 100 micrograms to about 750 mg, about 500 micrograms to about 400 mg, about 10 mg to about 250 mg, about 100 mg to about 900 mg, about 250 mg to about 750 mg, or about 400 mg to about 600 mg of *Citrobacter freundii* polypeptide, such as about 500 mg of *Citrobacter freundii* polypeptide. In other specific, non-limiting examples, a unit dosage contains from about 1 microgram per kilogram to about 500 milligrams per kilogram, about 100 micrograms per kilogram to about 5 milligrams per kilogram, or about 1 microgram per kilogram to about 50 micrograms per kilogram. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

VII Therapeutic Administration

The antimicrobial agents disclosed herein can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

In some examples, the agents are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. Particularly suitable administration routes are injection, infusion and direct injection into a target tissue.

In some embodiments, liposomes are used to deliver an antimicrobial agent to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369).

Appropriate doses of small molecule agents depend upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

VIII. Uses in Food Products

The presence of food spoilage organisms and pathogens in foods is a major concern to the food processing industry, government regulatory agencies, and consumers. Elimination of pathogenic contamination has been the subject of a great deal of study in the food industry and in the scientific community. There is a continued need to identify agents that are effective at reducing or eliminating microbial contamination of food products, especially in meat, poultry, and seafood products.

The antimicrobial agents disclosed herein are useful in imparting improved antibacterial activity to food products by inhibiting or retarding the growth of microbial organisms on food products. In one embodiment, a method is provided for inhibiting, or reducing, microbial growth in a food product, said method comprising applying an effective amount of the disclosed antimicrobial agent to the food product. Examples of food products include any food product susceptible to microbial degradation, including cooked or uncooked meat products, poultry products, seafood products, fruit, vegetables, grain products, and dairy foods.

Any suitable manner of applying the disclosed antimicrobial agent of this invention to the food product can be used. Examples of such methods include mixing an effective antimicrobial amount of the antimicrobial agent with the food product, injecting the antimicrobial agent into the food product, spreading a composition including the antimicrobial agent onto the outer surfaces of the food product, dipping the food product into a composition including the antimicrobial agent, spraying the food product with a composition including the antimicrobial agent, including an antimicrobial composition in a package with the food product such that the antimicrobial composition effectively covers the outer surfaces of the food product. The disclosed antimicrobial agent can be applied to the food either before or after cooking.

In some embodiments, the disclosed antimicrobial agent is administered to food in combination with a food preservative or other additive. In one embodiment, the disclosed antimicrobial agent is added to enhance the shelf-life of the food. In particular embodiments, the addition of the antimicrobial agent does not exert an adverse influence to the taste of the food. Additives applied to the food include, but are not limited to antibacterials, chelating agents, natural or synthetic seasonings, essential oils, and/or flavors, dyes and/or colorants, vitamins, minerals, nutrients, enzymes, binding agents such as guar gum and xanthan gum and the like.

The following examples are provided to illustrate certain particular features and/or embodiments. These examples should not be construed to limit the disclosure to the particular features or embodiments described.

EXAMPLES

Example 1

Isolation and Identification of a Bacteriocin with Antibacterial and Antibiofilm Activity from *Citrobacter freundii*

This example demonstrates the screening of a panel of over 100 bacterial strains to identify an agent secreted from *Citrobacter freundii* with antibacterial and antibiofilm activity.
Materials and Methods
Bacterial Strains, Media and Culture Conditions The bacteria used are listed in Table 1. Bacteria were grown routinely in LB medium at 37° C. *E. coli* strain WM3064 media was supplemented with 0.3 mM diaminopimelic acid (DAP). Cells were enumerated as colony-forming units (CFU) on LB agar plates. When appropriate, gentamicin was used at 10 μg/ml and kanamycin at 50 μg/ml.

TABLE 1

| Bacterial Strains Used | | |
|---|---|---|
| Name | Description | Source |
| *Citrobacter* | | |
| *C. braakii* ATCC 43162 | wild-type | ATCC |
| *C. braakii* ATCC 51113 | wild-type | ATCC |
| *C. freundii* NCTC 9750 | wild-type | ATCC |
| *C. freundii* ATCC 43864 | wild-type | ATCC |

TABLE 1-continued

Bacterial Strains Used

| Name | Description | Source |
|---|---|---|
| C. freundii ATCC 8090 | wild-type | ATCC |
| C. koseri ATCC 27156 | wild-type | ATCC |
| Cf-8A | cfbX mutant C. freundii ATCC 43864, bacteriocin defective | This work |
| C. freundii NCTC 9750-8A | C. freundii NCTC 9750 bearing plasmid pCfc1-8A | This work |
| C. freundii ATCC 8090-8A | C. freundii ATCC 8090 bearing plasmid pCfc1-8A | This work |
| Escherichia coli | | |
| E. coli S17-1 | Laboratory strain | |
| E. coli DH5α | Laboratory strain | |
| E. coli strain WM3064 | A diaminopimelic acid (DAP) auxotroph, derivative of strain B2155 | (Dehio, C., Meyer, M. 1997) |
| E. coli strain WM3064 | E. coli strain WM3064 bearing the mariner-based transposon delivery plasmid pBT20 | This work |
| E. coli S17-21pA | E. coli S17-1 bearing plasmid pCfc1-21pA | This work |
| E. coli S17-8A | E. coli S17-1 bearing plasmid pCfc1-8A | This work |
| E. coli S17 pMQ348 | pMQ124 + bacteriocin A-8 His$_8$ C-tag | This work |
| E. coli S17 pMQ124 | pMQ124 empty vector control | This work |
| E. coli S17-pRMQS345 | E. coli S17-1 + immune gene on pMQ131 | This work |

ATCC—American Type Culture Collection

Microbial Inhibition Assay.

To examine the ability of the tested bacteria to produce antimicrobial compounds, bacteria were grown for 18 hours in liquid broth. Thereafter, 20 μl of the overnight culture (~$10^8$ CFU/ml) was spotted on a lawn of microbial cells. Microbial lawns were prepared by spreading 100 μl of an overnight culture (for example, the organisms listed in Table 4) on an LB agar plate, and incubated at 37° C. Positive production of a diffusible antimicrobial compound was visualized by the inhibition of the susceptible microbial lawn and a clear zone surrounding the examined bacteria colony.

Crude Extraction of Antimicrobial Compound from C. freundii.

C. freundii was grown for 24 hours in broth at 37° C. One ml of the overnight culture was centrifuged for 3 minutes at 12,000 g. The supernatant was passed through a 0.2 μm pore-size filter. Ten μl of the filter-sterilized supernatant was spotted on a lawn of sensitive microbial cells and incubated for 24 hours at 37° C. Positive antimicrobial activity was visualized by the development of a zone of inhibition where the filter sterilized solution was spotted.

Construction C. freundii Transposon Mutant Library.

Transposon mutagenesis and mapping was performed as previously described (Medina et al., BMC Microbiol. 8:33, 2008). Recipient C. freundii ATCC 43864 was grown for 18 hours at 37° C. on a rotary shaker at 200 rpm in LB medium, to reach a final concentration of 1×$10^8$ cfu/ml. Donor E. coli strain WM3064 bearing the mariner-based transposon delivery plasmid pBT20 (Kulasekara et al., Mol Microbiol, 55:368-80, 2005) was grown to log phase ($A_{600}$=0.6-0.8). After incubating C. freundii at 42° C. for 10 minutes, 1 ml of the recipient was added to 0.25 ml of the donor in a 1.5 ml microfuge tube. The cells were pelleted in a microfuge, the medium decanted and the cells resuspended in 50 μl of LB, and the entire 50 μl was spotted on a LB plate containing 0.3 mM DAP and incubated at 37° C. for 24 hours. After incubation, the cells were scraped from the LB plate, resuspended in 1 ml of phosphate buffered saline (PBS), and 100 μl aliquots were plated on LB agar plates supplemented with gentamicin (10 μg/ml) to select for transposon recipients and lacking DAP to select against the E. coli. Plates were incubated at 37° C. until gentamicin-resistant (Gm$^r$) colonies developed. Thereafter, colonies were picked and placed into individual wells of a flat-bottom 96 well dish in 0.1 of ml LB and incubated at 37° C. for 24 hours before being frozen at −80° C. in a 20% v/v (volume/volume) glycerol solution. Using this method a library of ~4000 mutants was constructed.

Screening for Genes Involved in the Production of C. freundii Antimicrobial Compound.

To screen for mutants that are impaired in their ability to produce the antimicrobial compound, the C. freundii ATCC 43864 transposon mutant library was grown in LB medium for 24 hours. A 96-prong multi-well transfer device (Dan-Kar MC96) was used to transfer aliquots of mutant libraries onto plates containing lawns of sensitive C. freundii NCTC 9750. The plates were incubated at 37° C. for 24 hours. Positive or negative production of the antimicrobial compound was assessed by the formation of a zone of inhibition surrounding each mutant colony. C. freundii ATCC 43864 wild-type and PBS were used as positive and negative controls.

Molecular Techniques.

The DNA sequence flanking transposon mutants was determined using arbitrary polymerase chain reaction (PCR), as described previously (Medina et al., BMC Microbiol, 8:33, 2008). In brief, DNA flanking insertion sites are enriched in two rounds of amplification using primers specific to the ends of the transposon element and primers to the random sequence, which can anneal to chromosomal sequences flanking the transposon. In the first round, a primer unique to the right end of transposon elements (TnM Ext, 5'-ACAG-GAAACAGGACTCTAGAGG-3'; SEQ ID NO: 3) and 3 arbitrary primers (ARB1, 5'-GGCCACGCGTCGACTAG-TACNNNNNNNNNNNGATAT-3'; SEQ ID NO: 4) (ARB2, 5'-GGCCACGCGTCGACTAG-TACNNNNNNNNNNNACGCC-3'; SEQ ID NO: 5) (ARB3, 5'-GGCCACGCGTCGACTAG-TACNNNNNNNNNNNAGAG-3'; SEQ ID NO: 6) are used in 100 μl PCR reactions [10× New England Biolabs (NEB) polymerase buffer, MgSO$_4$ (1 mM), dNTPs (0.25 mM), and NEB Taq-DNA polymerase (5 U)] with 4 μl of chromosomal DNA purified from C. freundii mutants or wild-type C. freundii, using Puregene-Genomic DNA purification kit (5-PRIME ArchivePure DNA kit). The first-round reaction conditions were: (i) 2 minutes at 94° C.; (ii) 9×[30 seconds at 94° C., 30 seconds at 34° C., 2 minutes at 72° C.]; (iii) 20×[30 seconds at 94° C., 30 seconds at 54° C., 2 minutes at 72° C.]. The reactions for the second round of PCR were performed as described for the first round, except that 4 μl of the first-round PCR product was used as the source of DNA and the primers were ARB2 (5'-GGCCACGCGTCGACTAGTAC-3'; SEQ ID NO: 7) and TnM Int (5'-CACCCAGCTTTCTTGTACAC-3'; SEQ ID NO: 8). The ARB2 sequence is identical to the 5' end of the ARB1 primer, and the sequence of TnM Int is identical to the rightmost end of Tn5, near the junction between the transposon and the chromosome. The reaction conditions for the second round were 30×[30 seconds at 94° C., 30 seconds at 52° C., 3 minutes at 72° C.]. The PCR products were purified using the QIAquick Spin PCR purification kit (Qiagen), as described by the manufacturer. The PCR products were sequenced using the TnM Int primer at the Molecular Resource Facility, New Jersey Medical School and compared with the GenBank DNA sequence database using the BLASTX program.

The bacteriocin and immunity gene from plasmid pCfc1 were cloned using a recombineering technique using Saccharomyces cerevisiae (Shanks et al., Appl Environ Microbial, 72:5027-36, 2006). All plasmids used are listed in Table 2.

The bacteriocin gene was amplified using primers 2450 (accgcttctgcgttctgatttaatctgtatcaTTAGTGATGGTGGTGATGGTGGTGATGTGCAGG TCGGATTATTTC; SEQ ID NO: 9), and 2451 (ctctctactgtttctccatacccgtaggaggaaaaagaATGCCTGGATTTAATTATGGTG; SEQ ID NO: 10) that include an in-frame C-terminal polyhistidine (His7) tag (underlined), a sequence to target recombination with expression vector pMQ124 (Shanks et al., *Plasmid*, 62:88-97, 2009) (lower-case letters), and a sequence to amplify the bacteriocin gene (upper-case letters). The bacteriocin immunity gene was amplified using primers 2446 (cgttgtaaaacgacggccagtgccaagcttg-catgcctgcGTTTGATTAAAAGGCAGTGT; SEQ ID NO: 11) and 2447 (gaattgtgagcggataacaatttcacacaggaaacatATGAATGAACACTCAATAGATAC; SEQ ID NO: 12), with sequence to target recombination with pMQ131 (Shanks et al., *Plasmid*, 62:88-97, 2009) (lower-case letters), and sequence to amplify the bacteriocin immunity gene (upper-case letters). DNA was amplified with a high-fidelity polymerase (Phusion, New England Biolabs), using the manufacturer's directions. The recombination reactions place the amino-terminus tagged histidine-tagged under transcriptional control of the *E. coli* $P_{BAD}$ promoter on the ColE1-based pMQ124 vector, and places the immunity gene under transcriptional control of the *E. coli* $P_{lac}$ promoter on the pBBR1-based pMQ131 vector (Shanks et al., *Plasmid*, 62:88-97, 2009).

TABLE 2

Plasmids Used

| Name | Description | Source |
|---|---|---|
| pCfc1 | Bacteriocin bearing plasmid from *C. freundii* ATCC 43864 | This work |
| pCfc1-8A | pCfc1 with transposon mutation in cfbx | This work |
| pCfc1-21A | pCfc1 with transposon mutation intergenic region | This work |
| pBT20 | Mariner transposon delivery vector, oriR6K, bla, aacC1 | (Kulasekara, et al. 2005. *Mol Microbiol* 55: 368-80) |
| pMQ124 | Expression vector, oriColE1, oripRO1600, aacC1 | (Shanks et al. 2009. *Plasmid* 62: 88-9731) |
| pMQ131 | Broad host-range vector, oripBBR1, aphA-3 | (Shanks et al. 2009. *Plasmid* 62: 88-9731) |
| pMQ345 | pMQ131 + bacteriocin immunity gene from pCfc1 | This work |
| pMQ348 | pMQ124 + cfbx-His$_8$ | This work |

Purification of Polyhistidine-Tagged Bacteriocin from *E. coli*.

*E. coli* S17-1 harboring pMQ348 was grown for 18 hours in LB supplemented with 10 μg/ml gentamicin to reach a final concentration of $A_{600}$=0.2. One ml of the overnight culture was subcultured in 5 ml of fresh LB and left to grow for 2 hours, arabinose was added to the culture (0.2% final concentration) and the tubes were incubated for an additional 3 hours. To obtain crude cell proteins, the bacteria were pelleted by centrifugation, washed twice in PBS and resuspended in fresh 500 μl of PBS. To lyse the cells, cells were sonicated on ice for 50 seconds using a VC505 sonicator set on 80% strength (Sonics and Materials Inc., Newtown, Conn., USA). The cell debris was pelleted by centrifugation and the supernatant was removed and passed through a 0.2 μm pore-size filter (hereafter referred to as crude cell extract).

Immobilized metal ion affinity chromatography (IMAC) was used to further purify the His$_8$-tagged bacteriocin. The crude cell extract (1 ml) was mixed with 200 μl of Talon™ Metal Affinity Resin (Clontech Laboratories, Inc. Mountain View, Calif.) suspended washing-buffer (50 mM sodium phosphate, 300 mM NaCl and 10 mM imidazole pH-7). The mixture was stirred for 30 minutes, then centrifuged for 2 minutes at 1000×g. The pelleted resin was collected in a 2 ml tube and the unbound supernatant discarded. The resin was washed twice with washing-buffer containing 60 mM imidazole. Elution of the tagged protein was performed by adding 1 ml of washing-buffer supplemented with 200 mM imidazole (elution buffer). The eluent was incubated for 2 minutes, centrifuged for 2 minutes, and the supernatant containing the His$_8$-tagged protein was collected in a new tube. The sample was then filtered through a 0.2 μm pore-size filter (hereafter referred to as Ni IMAC-purified bacteriocin). Protein concentration was determined using Bio-Rad Quick Start™ Bradford protein assay, with bovine serum albumin (BSA) as standard.

Polyacrylamide gel electrophoresis (PAGE) and Western blot analysis were performed on each purification fraction using standard techniques. The PAGE gel (4-20% gradient) was a precast mini-format gel (Precise Protein Gel, Pierce), and a Bio-Rad Protean 3 device was used for running the gel and transfer to an Immobilon transfer membrane (Millipore). The blot was probed with a mouse-anti-polyhistine antibody (Covance product number MMS-156P), and the secondary antibody was a goat-anti-mouse horseradish peroxidase (HRP)-conjugated antibody (Pierce product number 32430).

Bacteriocin Anti-Microbial Activity.

To assess the antimicrobial activity of bacteriocin on planktonically grown bacteria, tested bacteria were grown for 18 hours at 37° C. Thereafter 1 ml of the cells were pelleted by centrifugation, washed and resuspended in 1 ml PBS. 100 μl cell aliquots were placed in a 2 ml microfuge tube and an equal volume of crude or IMAC-purified bacteriocin was added to the tube. Alternatively, as a control, 100 μl of sterile PBS was added to each tube. The tube was incubated at 37° C. for the duration of the experiment. Quantification of viable bacteria before and following treatment was performed by CFU enumeration. Each experiment was carried out at least three times.

Bacteriocin (CfbX) Anti-Biofilm Activity.

Biofilms were formed in a non-tissue culture treated, 96-well polyvinyl chloride microtiter dishes (Becton Dickinson, Franklin Lakes, N.J., USA) as previously described (Merritt et al., *Curr Protoc Microbiol*, Chapter 1:Unit 1B 1, 2005; and O'Toole et al., *Mol Microbiol*, 30:295-304, 1998). Briefly, microtiter wells were inoculated (100 μl per well) with 18-hours LB-bacteria that had been grown in cell culture to stationary phase in LB medium and diluted 1:100 in fresh LB media. *K. pneumoniae* biofilms were developed in M63 minimal salts supplemented with 1 mM $MgSO_4.7H_2O$, 14 mM $Na_3C_6H5O_7.2H_2O$, and 34 mM L-proline (Kadouri et al., *Appl Environ Microbiol*, 73:605-14, 2007); The plates were incubated for 18 hours at 30° C. to generate "preformed biofilms." Generally, "preformed" or "synthetic" biofilms are formed in liquid medium on a plastic surface (such as a culture dish, a culture flask, or a microtiter well) and in the absence of agar. To assess the antimicrobial activity of bacteriocin, the preformed biofilms were washed twice with PBS to remove planktonic cells and 100 μl of tested bacteriocin sample was added to each well. Alternatively, as a control, 100 μl of sterile PBS was added to the wells. The microtiter dishes were incubated at 30° C. for the duration of the experiment. Quantification of biofilm bacteria before and following treatment was performed by washing the microtiter plates with PBS, to remove non-adhering cells, 100 μl of fresh PBS was added to each well and the samples were sonicated for 8 seconds using a VC505 sonicator (Sonics and Materials Inc., Newtown, Conn., USA) followed by dilution plating and CFU enumeration (Kadouri et al., *Appl Environ Microbiol*, 71:4044-51, 2005; and Kadouri et al., *Appl Environ Microbiol,* 73:605-14, 2007). Each experiment was carried out at least three times.

Microscopy of biofilms was performed by first establishing biofilms on PVC cover slips in LB medium using the air liquid interface (ALI) method, described by Merritt et al. (*Curr Protoc Microbiol* 1B1.1-1B1.17, 2005). Biofilms of *C. freundii* ATCC 8090 were formed for 20 hours, non-adherant bacteria were removed by washing with PBS, then incubated in PBS with either crude lysates from S17-1+pMQ124 (empty vector) or S17-1+pMQ348 (colicin expressing plasmid) to a final concentration of 11.6 µg/ml total protein. After 60 minutes, biofilms were again washed with PBS and stained with a commercial live dead stain (Bac-Light, Invitrogen) according to the manufacturers specifications, and visualized with an Olympus Fluoview 1000 confocal laser scanning microscope (CLSM) and Fluoview 2.1 software.

Results

Identification of an Antimicrobial Compound Produced by *C. freundii* ATCC 43864.

In a screen aimed at isolating new antimicrobial compounds, 105 bacteria, representing 42 species and 26 different genera, were cross-examined in a microbial inhibition assay (for a full list of bacteria tested see Dashiff, et al., *J Appl Microbial,* 110:431-44, 2011).

One bacterial strain, *C. freundii* ATCC 43864, was found to produce a diffusible antimicrobial compound that inhibited the growth of other *C. freundii* strains (FIG. 1A, I) and other bacteria described below. Growing *C. freundii* ATCC 43864 in liquid broth and filter sterilizing the culture supernatant (crude extraction method) also yielded the antimicrobial compound (as demonstrated by the clear area on the lawn of *C. freundii* NCTC 9750; FIG. 1A, II), suggesting that the compound was present in the culture media and did not require a competing organism for induction.

Colonies and filter sterilized supernatant were used in a microbial inhibition assay to determine if additional members of the *Citrobacter* genus produce a similar antimicrobial compound, as well as to evaluate their sensitivity to the antimicrobial compound produced by *C. freundii* ATCC 43864, As described in Table 3, an antimicrobial compound was produced only by *C. freundii* ATCC 43864. The compound was shown to inhibit the growth of *C. braakii* ATCC 43162, *C. freundii* NCTC 9750 and *C. freundii* ATCC 8090, but was not active in inhibiting its producing strain *C. freundii* ATCC 43864.

To further characterize the antimicrobial compound, crude extracts were isolated from *C. freundii* ATCC 43864 and subjected to a number of challenges. The following treatments were used: storage at −20° C. for 16 weeks, heating for 15 minutes at 80° C., DNase-I treatment for 3 hours (120 µg/ml), proteinase-K or trypsin treatment for 3 hours (100 µg/ml), and filtration through a 10-100 kDa Microcon Centrifugal Filter Devices (Millipore, Billerica, Mass.). Treated extracts were spotted on a lawn of sensitive *C. freundii* NCTC 9750 to evaluate their antimicrobial activity. The antimicrobial compound was found to be resistant to DNase-I and freezing, and sensitive to protease activity and heat. The compound was also found to have a size of between 50 to 100 kDa. From this analysis, it was believed that the antimicrobial compound was a protein.

Construction of *C. freundii* ATCC 43864 Transposon Mutant Library, and Isolation of Mutants Defective in the Synthesis of the Antimicrobial Compound.

To isolate mutants defective in the synthesis of the antimicrobial compound, a mariner-based transposon was used to mutagenize *C. freundii* ATCC 43864. For isolating mutants impaired in their ability to synthesis the antimicrobial compound, a *C. freundii* transposon mutant library was grown in LB medium for 24 hours. Thereafter, a 96-prong multi-well transfer device was used to transfer aliquots of mutant libraries onto lawn of *C. freundii* NCTC 9750, which was found to be sensitive to the compound. The plates were incubated for 24 hours until a zone of inhibition was seen surrounding each mutant (FIG. 1B). Using this approach from ~4000 mutant colonies, a mutant unable to produce a zone of inhibition was isolated (FIG. 1C). This mutant was designated Cf-8A. No difference in growth rate was observed between Cf-8A mutants and the *C. freundii* recipient when grown in LB medium.

Mapping of Mutation Cf-8A to a Predicted Bacteriocin Gene, cfbX.

The Cf-8A transposon mutation was mapped using arbitrary PCR to base pair 456 of a predicted bacteriocin gene, that is approximately 99% identical at the DNA level to the colA gene of *C. freundii* strain CA31, also known as colA-CA31. The resulting predicted protein has one amino acid change compared to the previously identified ColA-CA31,

TABLE 3

Production of antimicrobial compound by *Citrobacter* spp.

| Citrobacter extracts tested | C. braakii ATCC 43162 | C. braakii ATCC 51113 | C. freundii NCTC 9750 | C. freundii ATCC 43864 | C. freundii ATCC 8090 | C. koseri ATCC 27156 | PBS control |
|---|---|---|---|---|---|---|---|
| *Citrobacter* tested | | | | | | | |
| *C. braakii* ATCC 43162 | − | − | − | + | − | − | − |
| *C. braakii* ATCC 51113 | − | − | − | − | − | − | − |
| *C. freundii* NCTC 9750 | − | − | − | + | − | − | − |
| *C. freundii* ATCC 43864 | − | − | − | − | − | − | − |
| *C. freundii* ATCC 8090 | − | − | − | + | − | − | − |
| *C. koseri* ATCC 27156 | − | − | − | − | − | − | − |

*Citrobacter* spp were grown in liquid broth for 24 hours. Cultures and filter-sterilized supernatants were cross-examined in a microbial inhibition assay for their ability to produce an antimicrobial compound as well as their sensitivity to *C. freundii* ATCC 43864. Antimicrobial activity was measured by the formation of a zone of inhibition around or at the point of inoculation. (+) Positive zone of inhibition. (−) No zone of inhibition.

specifically a leucine to serine substitution at amino acid 327. This newly isolated bacteriocin gene was named cfbX for *Citrobacter freundii* anti-biofilm factor x. It is also referred to as colA-43864. Bacteriocins are bacterial produced anti-microbial proteins, of which colicins are a sub-group.

Since the colA gene was found on a small plasmid that could replicate in *E. coli* (Morton et al., Gene, 17:317-21, 1982), it was tested whether the Cf-8A mutation was also on a plasmid. Plasmids were isolated from mutant strain Cf-8A and used to electroporate *E. coli*. Using the gentamicin resistance marker on the transposon as a selectable marker, gentamicin resistant *E. coli* colonies harboring the plasmid DNA from the Cf-8A were selected, supporting that the Cf-8A was on a plasmid.

A small plasmid, named pCfc1, was isolated from the WT ATCC 43864 strain and sequenced (Genbank Accession Number JF795024). Sequence analysis revealed that the plasmid is 6.72 kb in length, is ~99% identical to the pcolA plasmid of *C. freundii* strain CA31 (Morlon et al., Mol Gen Genet, 211:223-30, 1988), and has high similarity to bacteriocin-bearing plasmids from other *Citrobacter* species. The gene organization of pcolA (Morlon et al., Mol Gen Genet. 211:223-30, 1988) and the pCfc1 is identical, and includes a bacteriocin, a bacteriocin immunity protein, a lysis protein, and plasmid mobility genes.

Antimicrobial Activity of *E. coli* Harboring *C. freundii* ATCC 43864 Bacteriocin Plasmid (pCfc1)

In order to establish that the genes involve in the synthesis of the antimicrobial compound are plasmid-borne and that no additional genes are required for the production of the bacteriocin, the pCfc1 was mobilized into *E. coli*. To accomplish this, a selectable marker was moved onto the plasmid, by mutagenesis with the pBT20-derived mariner transposon. *C. freundii* ATCC 43864 cells containing pCfc1, were mutagenized with the mariner transposon. The prediction was that, in a small subset of the mutant colonies, the transposon would localize to the pCfc1 plasmid rather than the chromosome, thereby adding a selectable marker to the pCfc1 plasmid. Mutant *C. freundii* ATCC 43864 colonies were obtained, pooled, and plasmid DNA was isolated. The harvested plasmids were mobilized by electroporation into electrocompetent *E. coli* S17-1 cells. The S17-1 cells were plated on LB agar supplemented with gentamicin. One Gm$^r$ (gentamicin-resistant) isolate (*E. coli*-21pA) was selected for further analysis. DNA sequencing of purified plasmid from *E. coli*-21pA confirmed that the cell harbored pCfc1 containing a transposon insertion at position 441 in an intergenic region between two predicted entry exclusion genes. This mutation is not predicted to interfere with transcription of the bacteriocin gene. The marked plasmid was designated as pCfc1-21A.

*E. coli*-21pA, wild-type *E. coli* S17-1 (*E. coli* S17-1 bearing pCfc1-21A in which the pCfc1 plasmid has transposon inserted in an intergenic region), and *E. coli*-8A (*E. coli* S17-1 bearing pCfc1-8A in which the pCfc1 plasmid has a transposon mutation in the cfbx gene), were all spotted on a lawn of *C. freundii* NCTC 9750. As seen in FIG. 2 a clear zone of inhibition was seen around *E. coli*-21pA, demonstrating that the genes necessary for antimicrobial production are all present on pCfc1. No antimicrobial activity was seen on lawns that were inoculated with S17-1 bearing either an unrelated plasmid or the pCfc-8A plasmid (FIG. 2; *E. coli* wild-type and *E. coli* S17-8A respectively).

Production and Purification of Bacteriocin (Cfbx) in *E. coli*.

To determine whether the cfbx gene was sufficient for the observed antimicrobial phenotype, poly-histidine tagged versions of the gene (SEQ ID NOs: 16 and 18) were cloned and placed under control of an arabinose-inducible promoter. The His$_8$-tag was placed separately on the N- and C-termini of the Cfbx protein (SEQ ID NOs: 15 and 17, respectively), and while both conferred antimicrobial activity, the C-terminal version (SEQ ID NO: 17) exhibited higher relative antimicrobial activity, compared to the N-terminal version. Thus, further work was performed with the carboxy-terminal tagged version. To express cfbx in *E. coli*, pMQ348 (pMQ124-cfbx-His$_8$) was mobilized by electroporation into *E. coli* S17-1 cells, to make *E. coli* S17-pMQ348. As a control, *E. coli* S17-1 was also transformed with empty vector control pMQ124, to generate *E. coli* S17-pMQ124.

Figure 3:
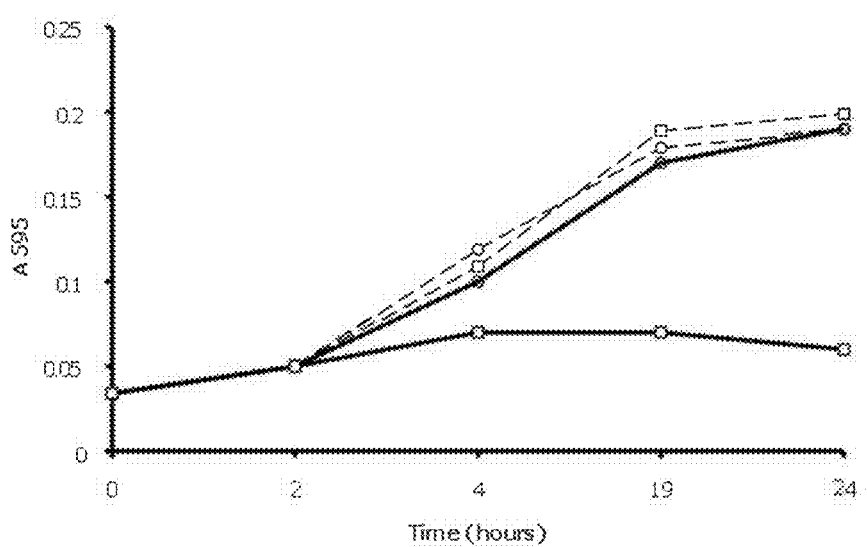
FIG. 3 is a graph showing the growth of *E. coli* S17-1 expressing CfbX-His$_8$. Cultures of *E. coli* S17-pMQ348 (full line) and empty vector control *E. coli* S17-pMQ124 (broken line) were grown at 37° C. in Lysogeny Broth (LB) supplemented with 0.2% glucose (inhibited condition, circle) or L-arabinose (inducing condition, square). Culture turbidity was measured by absorbance at $A_{595}$ nm to determine growth.

When grown in the presence of 0.2% glucose, no difference in growth was seen between *E. coli* S17-pMQ348 and *E. coli* S17-pMQ124 (FIG. 3). However, under promoter inducing conditions, when 0.2% L-arabinose was added to the media, a clear reduction in *E. coli* S17-pMQ348 growth was measured compared to the empty vector control (FIG. 3). These data suggest that expressing the cfbx gene in *E. coli* has a toxic effect on its host.

Figures 4A, 4B:
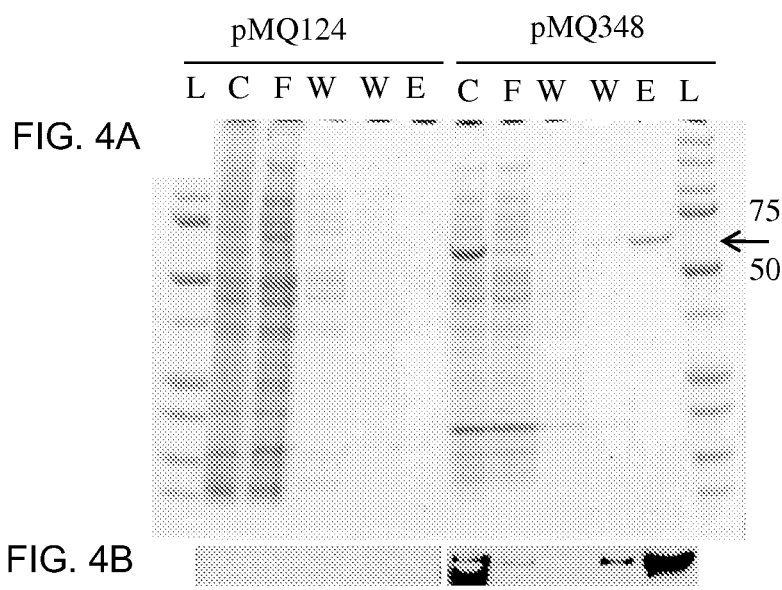
FIGS. 4A and 4B are a series of digital images showing the purification of CfbX-His$_8$.

To isolate crude extracts and pure Cfbx from *E. coli*, overnight cultures of *E. coli* S17-pMQ348 and empty vector control *E. coli* S17-pMQ124 were grown in the presence of arabinose and crude cell extract were prepared, as described above. Cfbx was isolated by IMAC, as described above. PAGE analysis showed the purification of a single protein of the predicted mass in the elution fraction of *E. coli* S17-pMQ348 lysates, whereas no band was observed with the empty vector control (FIG. 4A). To further confirm that the single band was the Cfbx-His$_8$ construct, Western blotting was performed and showed that the single eluted band observed on the PAGE gel was detected by an anti-polyhistidine antibody, whereas no bands were detected in the empty vector control (FIG. 4B).

Antimicrobial Activity of Crude Extract and Purified Cfbx-His$_8$.

Figure 5:
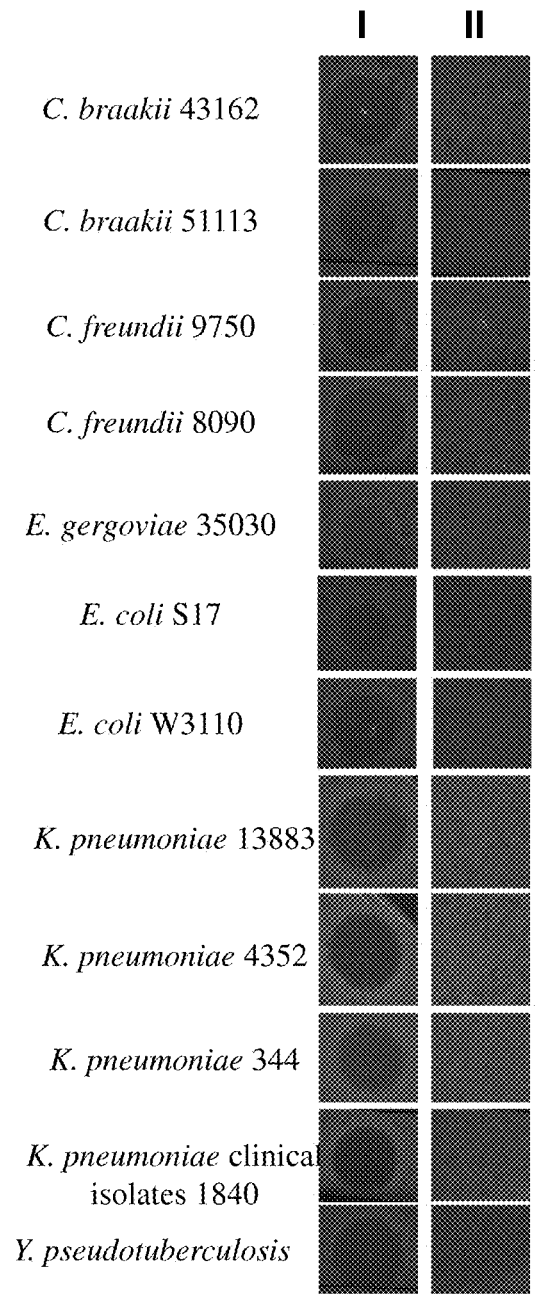
FIG. 5 is a series of digital images showing the antimicrobial activity of CfbX. Filter sterilized crude cell extracts from arabinose induced *E. coli* S17-pMQ348 (I) and empty vector control *E. coli* S17-pMQ124 (II) were prepared. 20 µl of the crude extracts (15 µg and 35 µg total protein from *E. coli* S17-pMQ348 and *E. coli* S17-pMQ124 respectively) were spotted on lawns of examined bacteria. Antimicrobial activity is seen by the formation of a zone of inhibition at the point of inoculation.

To assess the bacteriocin antimicrobial specificity, crude cell extracts from *E. coli* S17-pMQ348 and control *E. coli* S17-pMQ124 were prepared. 20 µl of the crude extracts were spotted on lawns of examined bacteria (15 µg and 35 µg total protein from *E. coli* S17-pMQ348 and *E. coli* S17-pMQ124, respectively). As seen in Table 4 and FIG. 5 the crude Cfbx-containing extract was able to inhibit the growth of a medically relevant bacteria from the family Enterobacteriaceae, including *C. braakii, C. freundii, Enterobacter gergoviae, E. coli, Klebsiella pneumoniae*, and *Yersini pseudotuberculosis*. Several other tested species were immune to the bacteriocin-containing extracts (Table 4 and FIG. 5). No inhibition was seen when crude protein extract from empty vector control *E. coli* S17-pMQ124 were spotted (FIG. 5 and Table 4, *E. coli* S17-pMQ124). Similar inhibition patterns were seen when *C. freundii* ATCC 43864 colonies were spotted on the lawns.

TABLE 4

Antimicrobial activity of bacteriocin.

| Bacteria tested | *E. coli* S17-pMQ348 | *E. coli* S17-pMQ124 |
|---|---|---|
| *Citrobacter* | | |
| *C. braakii* ATCC 43162 | + | − |
| *C. braakii* ATCC 51113 | + | − |
| *C. freundii* NCTC 9750 | + | − |
| *C. freundii* ATCC 43864 | − | − |
| *C. freundii* ATCC 8090 | + | − |
| *C. koseri* ATCC 27156 | − | − |

TABLE 4-continued

Antimicrobial activity of bacteriocin.

| Bacteria tested | E. coli S17-pMQ348 | E. coli S17-pMQ124 |
|---|---|---|
| *Enterobacter* | | |
| E. aerogenes ATCC 13048 | − | − |
| E. aerogenes ATCC 51697 | − | − |
| E. amnigenus ATCC 51816 | − | − |
| E. cloacae ATCC 700323 | − | − |
| E. cloacae ATCC 49141 | − | − |
| E. gergoviae ATCC 35030 | + | − |
| E. gergoviae ATCC 33028 | − | − |
| *Escherichia* | | |
| E. coli ZK2686/W3110 | + | − |
| E. coli S17-1 | + | − |
| E. coli DH5α | + | − |
| *Klebsiella* | | |
| K. pneumoniae ATCC 13883 | + | − |
| K. pneumoniae ATCC 4352 | + | − |
| K. pneumoniae ATCC 33495 | + | − |
| K. pneumoniae PIC 344 | + | − |
| K. pneumoniae clinical isolates LAB 1840 | + | − |
| K. pneumoniae clinical isolates LAB 1841 | − | − |
| K. pneumoniae clinical isolates LAB 1842 | − | − |
| K. pneumoniae clinical isolates LAB 1844 | + | − |
| K. pneumoniae clinical isolates LAB 1963 | + | − |
| K. pneumoniae clinical isolates LAB 1964 | − | − |
| K. pneumoniae clinical isolates LAB 1965 | − | − |
| K. pneumoniae clinical isolates LAB 1966 | − | − |
| K. pneumoniae clinical isolates LAB 1967 | + | − |
| *Morganella* | | |
| M. morganii ATCC 25829 | − | − |
| M. morganii ATCC 25830 | − | − |
| *Proteus* | | |
| P. mirabilis ATCC 35659 | − | − |
| P. mirabilis ATCC 43071 | − | − |
| P. mirabilis ATCC 25933 | − | − |
| P. mirabilis NCIMB 13283 | − | − |
| P. mirabilis ATCC 7002 | − | − |
| P. mirabilis PIC 366 | − | − |
| P. morganii PIC 3661 | − | − |
| P. rettgeri ATCC 9250 | − | − |
| P. vulgaris ATCC 33420 | − | − |
| P. vulgaris ATCC 49132 | − | − |
| P. vulgaris ATCC 8427 | − | − |
| P. vulgaris NCTC 4636 | − | − |
| P. vulgaris PIC 365 | − | − |
| Salmonella typhimurium PIC 3712 | − | − |
| Serratia marcescens PIC 361 | − | − |
| Shigella flexneri PIC 387 | − | − |
| *Yersinia* | | |
| Y. enterocolitica PIC 330 | − | − |
| Y. pseudotuberculosis PIC 399 | + | − |

Filter sterilized crude cell extracts from arabinose-induced *E. coli* S17-pMQ348 and *E. coli* S17-pMQ124 (empty vector control) were prepared. 20 µl of the crude extracts were spotted on lawns of examined bacteria (15 µg and 35 µg total protein from *E. coli* S17-pMQ348 and *E. coli* S17-pMQ124 respectively). Antimicrobial activity was measured by the formation of a zone of inhibition around or at the point of inoculation. (+) Positive zone of inhibition. (−) No zone of inhibition.
Bacteria source: PIC—Presque Isle Culture Collection, ATCC—American Type Culture Collection, LAB—lab collection.

Figure 6A:
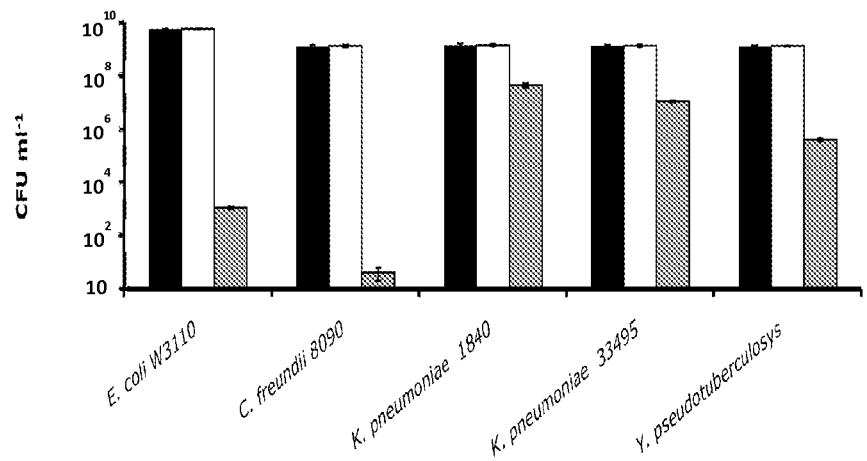
FIGS. 6A, 6B, and 6C are a series of graphs showing the antimicrobial activity of crude CfbX extract.

To assess the antimicrobial activity of bacteriocin on planktonic bacteria grown in broth, crude extracts, isolated from *E. coli* S17-pMQ348 (37 µg total protein) and control *E. coli* S17-pMQ124 (87 µg total protein), were added to overnight cultures. Incubating *C. freundii* and *E. coli* for 30 minutes with crude cell bacteriocin extracts had resulted in an 8 and 6 log reduction in cell viability. A more moderate 2-3 log reduction was measured for *K. pneumoniae* and *Y. pseudotuberculosis*. No reduction was seen after incubation with PBS or crude cell extracts isolated from *E. coli* S17-pMQ124 empty vector control (FIG. 6A).

Figure 6B:
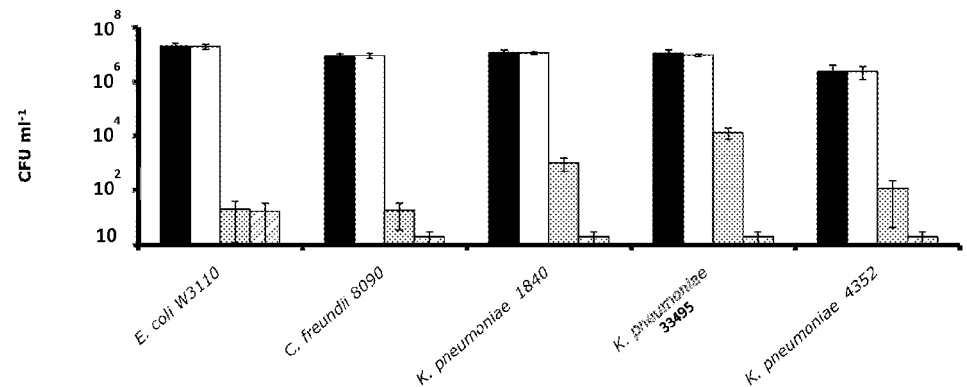

Whereas many antimicrobial agents are effective against planktonic cells, fewer are active against biofilms. Furthermore, it is not known whether bacteriocins have an inhibitory effect upon cells in a biofilm. However, when placed on biofilms, crude cell extracts, isolated from *E. coli* S17-pMQ348 (75 µg total protein) were surprisingly able to significantly reduce biofilm cell viability by up to 7 logs within 2 hours of incubation (FIG. 6B).

Figure 6C:
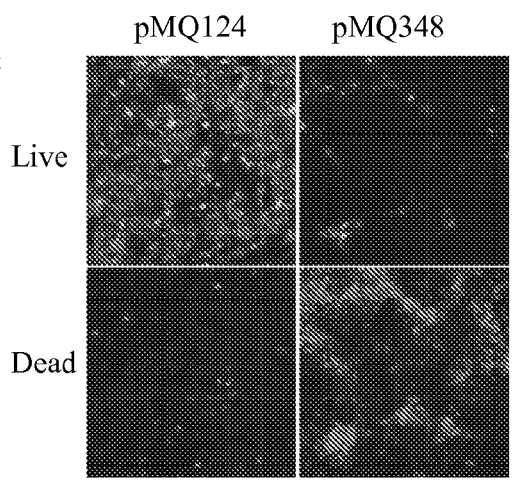

To further assess the antimicrobial effect of Cfbx on preformed biofilms, CLSM was used to analyze bacteriocin treated biofilms treated with live-dead fluorescent stains. Extracts from bacteria expressing recombinant Cfbx-His$_8$ had a clear bacteriocidal effect on *C. freundii* biofilm cells (FIG. 6C, pMQ348 Dead), whereas most the *C. freundii* biofilm exposed to extracts without the recombinant Cfbx-His$_8$ were largely composed of live cells (FIG. 5C, pMQ124 Live). Furthermore, the colicin exposed biofilms were stained red throughout the biofilms, suggesting that Cfbx is able to penetrate the biofilms.

Figure 7A:
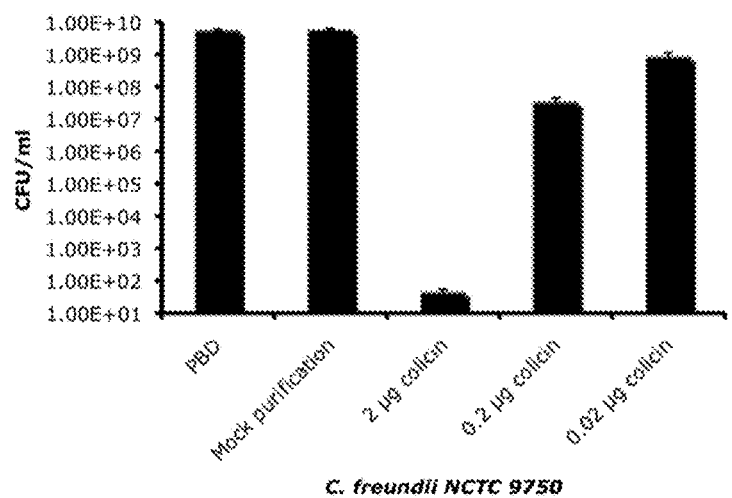
FIGS. 7A and 7B are a series of graphs showing antimicrobial activity of IMAC-purified CfbX.
Figure 7B:
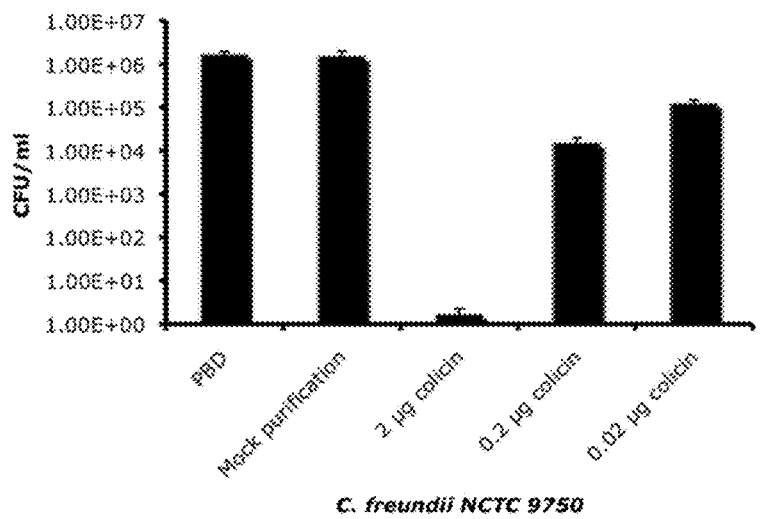

As was demonstrated for crude Cfbx extracts, incubating both planktonically grown bacteria and biofilms with a range of purified recombinant Cfbx-His$_8$ (2-0.02 µg), which was isolated from *E. coli* S17-pMQ348, had a profound effect on *C. freundii* NCTC 9750 cells. Incubating *C. freundii* with 2 µg of Cfbx-His$_8$ for 30 minutes had caused a 6-7 log reduction in planktonically grown and biofilm cell viability (FIG. 7A-B). The reduction in cell viability was dose dependent (FIG. 7A-B). In an additional experiment *K. pneumoniae* biofilms (composed of $2.5 \times 10^6$ CFU/ml) were incubated with 2 µg of Cfbx-His$_8$. A 2 log reduction ($1 \times 10^4$ CFU/ml) was seen within a 30 minute incubation period. No reduction was measured for *K. pneumoniae* biofilms incubated with control PBS or mock IMAC-purified protein isolated from *E. coli* S17-pMQ124 ($2.4 \times 10^6$ CFU/ml and $2.5 \times 10^6$ CFU/ml, respectively). Treating the bacteria with the elution buffer, which used to elute the IMAC-purified protein, also did not cause any cell reduction.

Expressing *C. freundii* Immunity Gene Provides Resistance from CfbX Antimicrobial Activity.

Figure 8A:
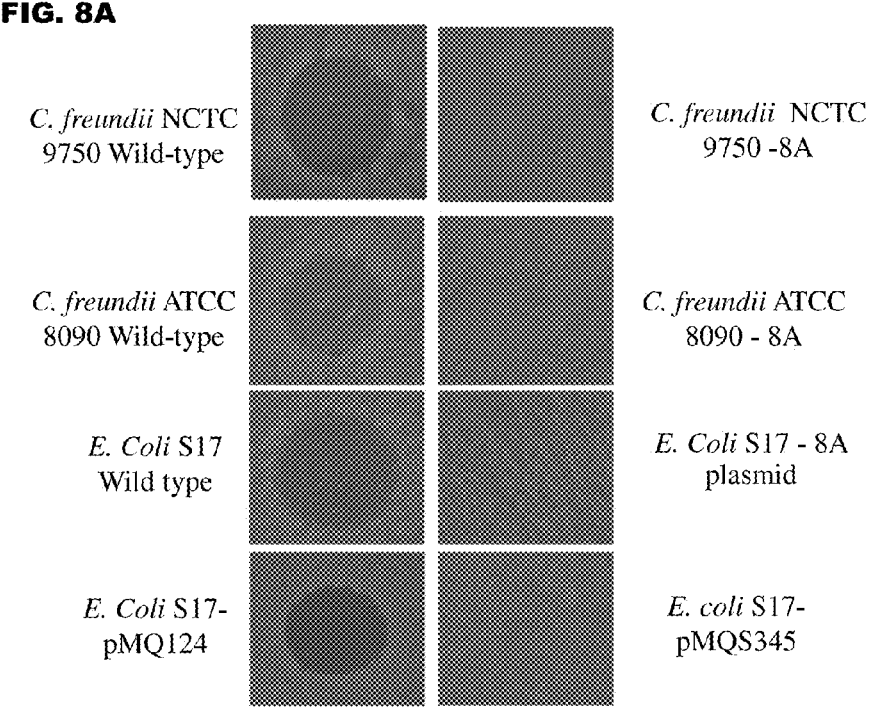
FIGS. 8A and 8B are a series of digital images and a graph showing the expression of the *C. freundii* immunity gene in bacteriocin sensitive bacteria.
Figure 8B:
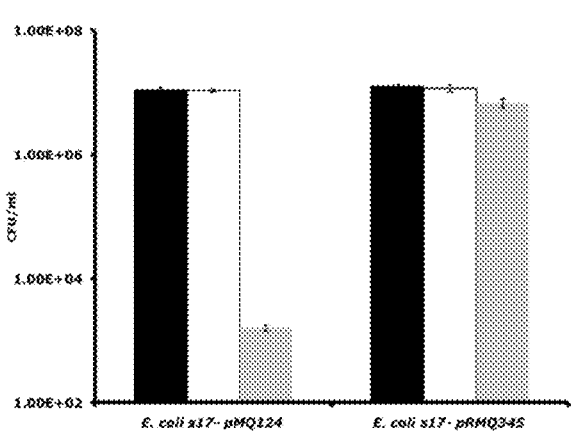

In order to investigate if the plasmid-borne immune gene, from *C. freundii* ATCC 43864, is capable of providing resistance to the antimicrobial activity of bacteriocin, bacteriocin-sensitive wild-type *E. coli* S17-1, *C. freundii* NCTC 9750 and *C. freundii* ATCC 8090 were transformed by electroporation with pCfc-8A with the mutated cfbX gene. The transformants were spread on an LB agar plate and 20 µl of crude Cfbx-containing extracts was spotted on top of each lawn (15 µg and 35 µg total protein from *E. coli* S17-pMQ348 and *E. coli* S17-pMQ124 respectively). As seen in FIG. 8A, cells harboring the bacteriocin defective plasmid, with an intact immune gene, were protected from Cfbx-containing extracts. In another experiment *E. coli* S17-1 was transformed with the immune gene, cloned under control of the *E. coli* P$_{lac}$ promoter on a multicopy plasmid, to yield strain *E. coli* S17-pRMQS345. As before, expressing the immune gene was sufficient to produce Cfbx resistant *E. coli* (FIG. 8A, *E. coli* S17-pRMQS345). CFU enumeration of planktonically grown bacteria also confirmed the resistance of *E. coli* S17-pRMQS345 to the antimicrobial effect of crude cell extracts containing CfbX (FIG. 8B).

Discussion

An antimicrobial protein from a *C. freundii* strain ATCC 43864 is identified in this disclosure using a genetic approach. The gene that codes for the antimicrobial agent, cfbX, is on a small plasmid almost identical in sequence to the colicin A producing plasmid from *C. freundii* strain CA31. The colA gene from *C. freundii* strain CA31 was previously described as type-A bacteriocin (Davies et al., *J Bacteria* 123:102-17, 1975), and used for several studies to characterize the role of "A" type bacteriocins (Crozel et al., *Mol Gen Genet,* 192:500-5, 1983; and Varenne et al., *Eur J Biochem,* 116:615-20, 1981). Based on the ~99% sequence identity, the biofilm-controlling CbfX described herein is also an "A" type bacteriocin. This group of bacteriocins gains access to bacterial cells through binding to a complex of outer membrane proteins (OmpF and BtuB) and lipopolysaccharides (Cascales, *Microbial Mol Biol Rev,* 71:158-229, 2007; and Chai et al., *J Bacteriol,* 151:983-8, 1982), then moves through the periplasmic space with the aid of TolA and TolB (Hecht et al., *FEBS Lett,* 584:2249-52, 2010) and kills bacteria by disrupting their membrane and uncoupling the proton gradient (Cascales, *Microbial Mol Biol Rev,* 71:158-229, 2007; and Schein et al., *Nature,* 276:159-63, 1978).

The plasmid pCfc1-21A was able to replicate in *E. coli* and was sufficient to confer antimicrobial activity to *E. coli*; however, when the predicted bacteriocin gene was mutated with a transposon, no antimicrobial activity was observed, suggesting that the antibacterial requires the cfbX gene. To further confirm that the bacteriocin gene is necessary and sufficient for the antimicrobial activity, the cfbX gene was cloned and expressed in *E. coli* under control of an arabinose inducible promoter. Induction of the cfbX gene resulted in a severe growth defect, supporting that expression of the cfbX gene alone is toxic to the host cell. Crude fractions from the *E. coli* strain bearing pMQ348, but not the empty vector control exhibited antimicrobial activity against several genera of Gram-negative bacteria including important pathogens *K. pneumoniae* and *E. coli*. Interestingly, only 8 out of 13 *K. pneumoniae* isolates exhibited sensitivity to the colicin. While bacteriocin resistance can arise from mutation of surface receptors and periplasm translocators, there is a cost to the cells. For example, loss of BtuB confers defects in uptake of vitamin B12 (Kadner et al., *J Bacteriol,* 115:514-21, 1973), which could confer growth defects under some conditions. An alternative possibility for resistance by five of the *K. pneumoniae* isolates, is that some or all of the resistant strains harbor bacteriocin immunity genes. It is also demonstrated herein that the plasmid pCfc1-8A or the immunity protein gene alone, expressed on a multicopy plasmid, was able to provide protection from CfbX. This result further supports that the antimicrobial effect was specific to the CfbX, rather than some unrelated compound induced by expression of the CfbX.

It is surprisingly demonstrated herein that purified bacteriocin can effectively and rapidly kill cells in biofilms in a dose dependent manner and that bacteriocins can be used to treat bacterial biofilms, either by themselves or coupled with other antimicrobials and biocontrol agents, such as phage and predatory bacteria, and to optimize methods for destroying established biofilms.

Example 2

Treatment of a Subject Having a Bacterial Infection

This example describes methods that can be used to treat a subject with a bacterial infection. However, one skilled in the art will appreciate based on the teachings herein that methods that deviate from these specific methods can also be used to successfully treat a subject with a bacterial infection.

In an example, a subject having a bacterial infection is identified and selected for treatment. In some examples, the subject is identified because of clinical symptoms associated with a bacterial infection (for example, but not limited to, fever, malaise, pain, redness, nausea, vomiting, diarrhea, swelling, cough, or elevated white blood cell count) or because the indwelling device is not operating properly (for example, but not limited to, occlusion of a catheter). Patients may be selected for treatment based on clinical judgment, or by performing in vitro assays of antimicrobial sensitivity before initiating treatment. In some instances, the patient may be infected with an antibiotic-resistant bacteria. In other instances, the patient may be infected with a biofilm. In particular cases, the biofilm may be on a living surface (for example, a bone, a joint, an organ, an organ cavity, or a tissue of the subject) or a non-living surface (for example, an implanted medical device) in the subject.

Following subject selection, a therapeutically effective amount of an antibacterial agent (for example, a *Citrobacter freundii* colicin A polypeptide, or a variant thereof) is administered to the subject. The amount of the composition administered depends on the subject being treated, the severity of the infection, and the manner of administration of the therapeutic composition. Ideally, a therapeutically effective amount of an agent is the amount sufficient to reduce, and/or inhibit the growth or multiplication of, and/or treat the infection in a subject without causing a substantial cytotoxic effect in the subject.

A reduction in the clinical symptoms associated with the infection, for example, reduced fever or reduced white blood cell count, or improved operation of the implanted device, indicates the effectiveness of the treatment.

Example 3

Treatment of a Biofilm

This example describes methods that can be used to treat a biofilm. However, one skilled in the art will appreciate, based on the teachings herein, that methods that deviate from these specific methods can also be used to successfully treat a biofilm.

In an example, a non-living or living surface infected with a biofilm is identified and selected for treatment. In a specific, non-limiting example, a medical device infected with a biofilm is identified and selected for treatment. In particular examples, the medical device is identified because (i) it is located in a subject (an indwelling device) and the subject is experiencing clinical symptoms associated with a bacterial infection (for example, but not limited to, fever, malaise, pain, redness, nausea, vomiting, diarrhea, swelling, cough, or elevated white blood cell count), (ii) an indwelling device is not operating properly (for example, but not limited to, occlusion of a catheter), or (iii) routine testing of the medical device identified a bacterial contamination. A medical device, or patients having a medical device, may be selected for treatment by performing in vitro assays of antimicrobial sensitivity before initiating treatment. Patients having a medical device may be further selected based on clinical judgment. In some instances, the device, or the patient having the device, may be infected with an antibiotic-resistant bacteria. In other instances, the device, or the patient having the device, may be infected with a biofilm. In particular cases, the biofilm may be on a surface of an implanted medical device located in the subject (for example, a device partially or wholly inserted or surgically implanted in the subject). In other embodiments, the biofilm may be on a medical device located external to the patient. In some embodiments, the medical device is not implanted, nor does it have direct therapeutic activity. The device can be, for example, a storage device, such as a medical storage device, for example a container for a contact lens.

Following selection of the device needing treatment, an effective amount of an antibacterial agent (for example, a *Citrobacter freundii* colicin A polypeptide, or a variant thereof) is administered to the device. The amount of the composition administered depends on the device being treated, the severity of the infection, and the manner of administration of the composition. Ideally, an effective amount of an agent is the amount sufficient to reduce, and/or inhibit the growth or multiplication of, and/or treat the infection on the device. An improvement in the operation of the device, or a decrease in the number of bacteria contaminating the device, indicates the effectiveness of the treatment.

Alternatively, following selection of a subject having a contaminated device, a therapeutically effective amount of an antibacterial agent (for example, a *Citrobacter freundii* colicin A polypeptide, or a variant thereof) is administered to the subject. The amount of the composition administered depends on the subject being treated, the severity of the infection, and the manner of administration of the therapeutic composition. Ideally, a therapeutically effective amount of an agent is the amount sufficient to reduce, and/or inhibit the growth or multiplication of, and/or treat the infection on the device in a subject without causing a substantial cytotoxic effect in the subject. A reduction in the clinical symptoms associated with the infection, for example, reduced fever or reduced white blood cell count, or improved operation of the implanted device, indicates the effectiveness of the treatment.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An isolated polypeptide, comprising the amino acid sequence set forth as SEQ ID NO: 1, wherein the polypeptide has an antibacterial activity against a biofilm.

2. A composition comprising the polypeptide of claim 1.

3. The composition of claim 2, further comprising one or more compounds selected from the group consisting of a carrier, diluent, adjuvant, solubilizing agent, and suspending agent.

4. The composition of claim 2, further comprising a second antibacterial agent, an antifungal agent, or an antiprotozoal agent.

5. A pharmaceutical composition, comprising the polypeptide of claim 1 and a pharmaceutical carrier.

6. A medical device comprising a surface, wherein the surface comprises an antimicrobial effective amount of the polypeptide of claim 1.

7. The medical device of claim 6, wherein the polypeptide is incorporated into a polymeric coating on the medical device surface.

8. A method for treating a biofilm, comprising contacting the biofilm with an effective amount of an antibacterial agent, wherein the agent comprises the isolated polypeptide of claim 1 and wherein the isolated polypeptide has an antibacterial activity against the biofilm, thereby treating the biofilm.

9. The method of claim 1, further comprising selecting for treatment a surface infected with a biofilm.

10. The method of claim 1, wherein the biofilm is on a medical device suitable for surgical implantation within the body.

11. The method of claim 10, wherein the medical device is a catheter, a stent, a shunt, an endotracheal tube, a gastric feeding tube, a prosthetic joint, an intrauterine device, a voice prosthesis, a central venous catheter, a tympanostomy tube, a prosthetic heart valve, or a pacemaker.

12. The method of claim 1, wherein treating the biofilm reduces biofilm cell viability by at least 2%, at least 5%, at least 10%, at least 20%, at least 25%, at least 50%, at least 75%, at least 80%, at least 90%, at least 95%, at least 99%, or 100%.

13. The method of claim 1, wherein the biofilm comprises Gram-negative bacteria.

14. The method of claim 13, wherein the Gram-negative bacteria comprise the family Enterobacteriacae.

15. The method of claim 14, wherein the Enterobacteriacae bacteria comprise a genus selected from the group consisting of *Citrobacter, Enterobacter, Escherichia, Klebsiella*, and *Yersinia*.

16. The method of claim 12, further comprising one or more additional administrations of the isolated polypeptide to inhibit growth of the biofilm.

17. The method of claim 1, further comprising contacting the biofilm with an effective amount of a second antibacterial agent.

18. The method of claim 1, further comprising contacting the biofilm with an effective amount of an antifungal agent or an antiprotozoal agent.

19. A method for treating a subject infected with a biofilm, comprising: administering to the subject a therapeutically effective amount of a pharmaceutical composition comprising an antibacterial agent, wherein the antibacterial agent comprises the isolated polypeptide of claim 1 and wherein the isolated polypeptide has an antibacterial activity against the biofilm, thereby treating the subject.

20. The method of claim 19, wherein the biofilm is on a medical device implanted in the subject.

21. The method of claim 20, wherein the medical device is a catheter, a stent, a shunt, an endotracheal tube, a gastric feeding tube, a prosthetic joint, an intrauterine device, a voice prosthesis, a central venous catheter, a tympanostomy tube, a prosthetic heart valve, or a pacemaker.

22. The method of claim 19, wherein treating the subject reduces biofilm cell viability by at least 2%, at least 5%, at least 10%, at least 20%, at least 25%, at least 50%, at least 75%, at least 80%, at least 90%, at least 95%, at least 99%, or 100%.

23. The method of claim 22, further comprising one or more additional administrations of the pharmaceutical composition to the subject to inhibit further growth of the bacterial biofilm.

24. The method of claim 19, wherein the biofilm comprises Gram-negative bacteria.

25. The method of claim 24, wherein the Gram-negative bacteria comprise the family Enterobacteriacae.

26. The method of claim 25, wherein the bacteria comprises a genus selected from the group consisting of *Citrobacter, Enterobacter, Escherichia, Klebsiella*, and *Yersinia*.

27. The method of claim 19, further comprising administering to the subject a therapeutically effective amount of a second antibacterial agent.

28. The method of claim 19, further comprising administering to the subject a therapeutically effective amount of an antifungal agent or an antiprotozoal agent.

* * * * *